United States Patent [19]

Zalipsky et al.

[11] Patent Number: 5,219,564
[45] Date of Patent: Jun. 15, 1993

[54] POLY(ALKYLENE OXIDE) AMINO ACID COPOLYMERS AND DRUG CARRIERS AND CHARGED COPOLYMERS BASED THEREON

[75] Inventors: Samuel Zalipsky, Princeton; Durgadas bolikal, Edison; Aruna Nathan, Piscataway; Joachim B. Kohn, Highland Park, all of N.J.

[73] Assignee: Enzon, Inc., South Plainfield, N.J.

[21] Appl. No.: 726,301

[22] Filed: Jul. 5, 1991

Related U.S. Application Data

[63] Continuation-in-part of Ser. No. 549,494, Jul. 6, 1990, abandoned.

[51] Int. Cl.$^5$ .................. A61K 31/74; A61K 39/00; C08G 69/08
[52] U.S. Cl. .................. 424/78.17; 424/78.08; 424/85.5; 424/85.8; 530/390.1; 530/391.7; 530/810; 528/310
[58] Field of Search .................. 424/78.08, 85.8, 85.5, 424/78.17; 530/390.1, 391.7; 528/310

[56] References Cited

U.S. PATENT DOCUMENTS

| | | | |
|---|---|---|---|
| 4,179,337 | 12/1979 | Davis et al. | 530/816 |
| 4,275,000 | 6/1981 | Ross | 424/85.8 |
| 4,388,441 | 6/1983 | Katz | 525/54.1 |
| 4,460,560 | 7/1984 | Tokes et al. | 424/78.17 |
| 4,680,338 | 7/1987 | Sundoro | 525/54.1 |
| 4,843,147 | 6/1984 | Levy et al. | 424/85.8 |
| 4,863,735 | 9/1989 | Kohn et al. | 424/422 |
| 4,892,733 | 1/1990 | Bichon et al. | 424/422 |
| 4,919,928 | 4/1990 | Jansen et al. | 424/85.8 |
| 4,931,287 | 6/1990 | Bae et al. | 424/484 |
| 5,091,176 | 2/1992 | Braatz et al. | 424/78.17 |

OTHER PUBLICATIONS

Graham et al., *Makromol. Chem., Macromol. Symp.*, 19, 255–73 (1988).
Imai et al., *Makromol. Chem., Rapid Commun.*, 5, 47–51 (1984).
Wang et al., *J. Macromol. Sci.-Chem.*, A26(2–3), 505–18 (1989).
Ouchi et al., *J. Macromol. Sci.-Chem.*, A24(9), 1011–32 (1987).
Bos et al., *Acta Pharm. Technol.*, 33(3), 120–5 (1987).
Pretula et al., *Makromol. Chem., Rapid Commun.*, 9, 731–7 (1988).
Jeon et al., *J. Polym. Sci. Part A Polym. Chem.*, 27, 1721–30 (1989).
Cho et al., *Makromol. Chem.*, 191, 981–91 (1990).
Kimura et al., *Makromolecules*, 16, 1023–4 (1983).

*Primary Examiner*—Thurman K. Page
*Assistant Examiner*—Peter F. Kulkosky
*Attorney, Agent, or Firm*—Lerner, David, Littenberg, Krumholz & Mentlik

[57] ABSTRACT

Copolymers of poly(alkylene oxides) and amino acids or peptide sequences are disclosed, which amino acids or peptide sequences have pendant functional groups that are capable of being conjugated with pharmaceutically active compounds for drug delivery systems and cross-linked to form polymer matrices functional as hydrogel membranes. The copolymers can also be formed into conductive materials. Methods are also disclosed for preparing the polymers and forming the drug conjugates, hydrogel membranes and conductive materials.

20 Claims, 1 Drawing Sheet

POLY(ALKYLENE OXIDE) AMINO ACID COPOLYMERS AND DRUG CARRIERS AND CHARGED COPOLYMERS BASED THEREON

This is a continuation-in-part of application Ser. No. 07/549,494, filed Jul. 6, 1990, abandoned, the disclosure of which is hereby incorporated herein by reference thereto.

BACKGROUND OF THE INVENTION

The present invention relates to copolymers of poly(alkylene oxides) and amino acids or peptide sequences, and more particularly to copolymers of polyalkylene oxides such as polyethylene glycol (PEG), with amino acids or peptide sequences. The present invention also relates to conjugates of such polymers formed with pharmaceutically active compounds covalently bonded to the amino acid or peptide sequence of the copolymer. The present invention further relates to ionically conductive materials, hydrogel membranes and semi-interpenetrating polymer networks prepared from the copolymers of the present invention.

The conjugation of biologically active polypeptides with water-soluble polymers such as PEG is well-known. The coupling of biologically active and pharmaceutically active peptides and polypeptides to PEG and similar water-soluble polymers is disclosed by U.S. Pat. No. 4,179,377 to Davis et al. Polypeptides modified with PEG are disclosed as exhibiting dramatically reduced immunogenicity and antigenicity. The PEG conjugates also exhibit a wide range of solubilities and low toxicity, and have been shown to remain in the bloodstream considerably longer than the corresponding native compounds yet are readily excreted. The PEG conjugates have also been shown not to interfere with enzymatic activity in the bloodstream or the conformation of the polypeptides conjugated thereto. Accordingly, a number of PEG-conjugates of therapeutic proteins have been developed exhibiting reduced immunogenicity and antigenicity and longer clearance times, while retaining a substantial portion of the protein's physiological activity.

Attention has also focused upon the conjugation of PEG with therapeutic drugs. Gnanov et als., *Macromolecules*, 17, 945-52 (1984) observed that the attachment of PEG to various drugs led to prolonged pharmacological activity.

As disclosed in the above-cited U.S. Pat. No. 4,179,337, the conjugation of PEG begins with functionalization of the terminal hydroxyl groups of the polymer prior to coupling with a ligand of biological relevance, although some ligands are capable of covalently bonding to the terminal hydroxyl groups without functionalization. The foregoing is also disclosed in Zalipsky et al., *J. Macromol. Sci-Chem.*, A21, 839-845 (1984); and Zalipsky et al., *Eur. Polym. J.*, 19, 1177-1183 (1983). One of the limitations of PEG is that it has only two reactive end groups available for functionalization. This is a particularly severe design limitation for PEG chains of high molecular weight which contain only a very small number of reactive groups for any given weight of polymer. To circumvent this problem, several reaction schemes have been disclosed in which PEG chains were copolymerized with a variety of difunctional co-monomers. For example, Graham et al., *Makromol. Chem. Macromol. Symp.*, 19, 255-73 (1988) and Imai et als., *Makromol. Chem. Rapid. Commun.*, 5, 47-51 (1984) disclose copolymers of poly(oxyethylene) dicarboxylic acids with aliphatic and aromatic amines. Block copolymers of PEG with polyesters are disclosed by Wang et als., *J. Macromol Sci-Chem.*, A26(2&3), 505-18 (1989). Block copolymers of PEG with poly(L-proline) are disclosed by Jeon et als., *J. Polym. Sci. Part A Polym. Chem.*, 27, 1721-30 (1989). Block copolymers of PEG with poly(gamma-benzyl L-glutamate) are disclosed by Cho et al., *Makromol. Chem.*, 191, 981-91 (1990). In these references, the use of the PEG block copolymers as biomaterials is suggested. Polyethylene glycols, cross-linked by copolymerization with triols and diisocyanates for use in the preparation of hydrogels and hydrogel membranes are disclosed by Kimura et als., *Macromolecules*, 16, 1024-6 (1983), Ouchi et als., *J. Macromol. Sc.-Chem.*, A24(9), 1011-32 (1987), and Bos et al., *Acta Pharm Technol.*, 33(3), 120-5 (1987). The hydrogel and hydrogel membranes have been investigated as potential materials for controlled drug delivery. However, none of the above-disclosed PEG copolymers have the desirable structural feature of having multiple functional groups at regular, predetermined intervals that can be utilized for drug attachment or cross-linking reactions.

The preparation of PEG ionomers with phosphate diester linkages is disclosed by Pretula et als., *Macromol. Chem. Raoid Commun.*, 9, 731-7 (1988), the apparently only known example of a strictly alternating copolymer of PEG. However, the reaction schemes developed by Pretula require highly reactive intermediates that need to be handled with extreme care. Consequently, the resulting copolymers have apparently not yet found any practical applications.

PEG copolymers having multiple pendant functional groups at regular predetermined intervals that can be utilized for drug attachment or cross-linking reactions would be highly desirable.

SUMMARY OF THE INVENTION

These needs are met by the present invention, which provides copolymers of poly(alkylene oxides) and amino acids or peptide sequences, which amino acids or peptide sequences provide pendant functional groups at regular intervals within the polymer for drug attachment or cross-linking reactions. The resulting polymer is dominated by the desirable properties of PEG, while the amino acid or peptide sequences provide biocompatible moieties having pendant functional groups for drug attachment or cross-linking.

Therefore, in accordance with one aspect of the present invention, polymers are provided that are copolymers of a poly(alkylene oxide) and an amino acid or peptide sequence. In a first embodiment of this aspect of the invention, a polymer is provided in which the poly(alkylene oxide) and amino acid or peptide sequence are copolymerized by way of hydrolytically stable urethane linkages. The polymer contains one or more recurring structural units independently represented by Formula I:

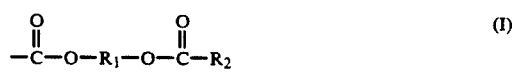

In Formula I, $R_1$ is a poly(alkylene oxide), and $R_2$ is an amino acid or peptide sequence containing two amino groups and at least one pendant carboxylic acid group. The pendant carboxylic acid group is not involved in the polymerization process and is thus retained as a pendant group on the polymer. This pendant functional group can be further derivatized (e.g., converted to a different functional group), used for crosslinking or for the attachment of ligands, e.g., drugs Preferably, $R_2$ is represented by Formula II:

$$-R_5-(R_3)_a-\underset{\underset{D}{|}}{CH}-(R_4)_b-R_5- \qquad (II)$$

$R_3$ and $R_4$ are independently selected from saturated and unsaturated, straight-chained and branched alkyl groups containing up to 6 carbon atoms and alkyl phenyl groups, the alkyl portions of which are covalently bonded to an amine and contain up to 6 carbon atoms. The values for a and b are independently zero or one. $R_5$ is independently selected from —NH— or —NH—AA—, wherein —AA— is an amino acid or peptide sequence, with the proviso that —AA— has a free N-terminus. D is a pendant functional group having a structure represented by $$-\overset{O}{\underset{||}{C}}-Y \text{ OR } -\overset{O}{\underset{||}{C}}-X-Y.$$

When D is $$-\overset{O}{\underset{||}{C}}-Y.$$

Y is selected from —OH, —NH—NH$_2$, —O—R$_6$—NH$_2$, —O—R$_6$—OH, —NH—R$_6$—NH$_2$, —NH—R$_6$—OH, $$-NH-R_6-\overset{O}{\underset{||}{C}}-OH, -O-R_6-\overset{O}{\underset{||}{C}}-OH,$$

a C-terminus protecting group and a derivative of a pharmaceutically active compound covalently bonded to the pendant functional group by means of an amide bond in the case when in the underivatized pharmaceutically active compound a primary or secondary amine is present at the position of the amide bond in the derivatives; or an ester bond in the case when in the underivatized pharmaceutically active compound a primary hydroxyl is present at the position of the ester bond in the derivative. When D is $$-\overset{O}{\underset{||}{C}}-X-Y,$$

Y is a derivative of a pharmaceutically active compound covalently bonded to the pendant functional group by means of X, wherein X is a linkage selected from —NH—NH— in the case when in the underivatized pharmaceutically active compound an aldehyde or ketone is present at the position linked to the pendant functional group by means of X; —NH—NH—, —NH—R$_6$—NH—, —O—R$_6$—NH—, —O—R$_6$—O— or —NH—R$_6$—O— in the case when in the underivatized pharmaceutically active compound a carboxylic acid is present at the position linked to the pendant functional group by means of X; and $$-O-R_6-\overset{O}{\underset{||}{C}}- \text{ or } -NH-R_6-\overset{O}{\underset{||}{C}}-$$

in the case when in the underivatized pharmaceutically active compound a primary or second amine or primary hydroxyl is present in the position linked to the pendant functional group by means of X. $R_6$ is selected from alkyl groups containing from two to six carbon atoms, aromatic groups, alpha-, beta-, gamma- and omega- amino acids, and peptide sequences.

In a second embodiment of this aspect of the invention, a polymer is provided in which a terminal amino groups and an amino acid or peptide sequence are copolymerized by way of hydrolytically stable amide linkages in the case of the poly(alkylene oxide) having terminal amino groups, and by way of hydrolyzable ester linkages in the case of poly(alkylene oxides) having terminal hydroxyl groups.

The polymer contains one or more recurring structural units independently represented by Formula III:

$$-L-R_1-L-R_2- \qquad (III)$$

$R_1$ is a poly(alkylene oxide), L is —O— or —NH— and $R_2$ is an amino acid or peptide sequence containing two carboxylic acid groups and at least one pendant amino group. As with the pendant group of Formula I, the pendant amino group is not involved in the polymerization process and is thus retained as a pendant group on the polymer that can be further derivatized, used for crosslinking, or for the attachment of ligands. Preferably $R_2$ is represented by Formula IV:

$$-R_5-(R_3)_a-\underset{\underset{D}{|}}{CH}-(R_4)_b-R_5- \qquad (IV)$$

$R_3$, $R_4$, a and b are the same as described above with respect to Formula II. $R_5$ is independently $$-\overset{O}{\underset{||}{C}}-, \text{ or } -\overset{O}{\underset{||}{C}}-AA-$$

wherein —AA— is an amino acid or peptide sequence, with the proviso that —AA— has a free C-terminus.

D is a pendant functional group representing either —NHZ or —NH—X$_1$—Z. When D is —NHZ, Z is hydrogen, $$-\overset{O}{\underset{||}{C}}-R_6-NH_2, -\overset{O}{\underset{\backslash\backslash}{C}}-R_6-OH, -\overset{O}{\underset{\backslash\backslash}{C}}-R_6-\overset{O}{\underset{\backslash\backslash}{C}}-OH,$$

an N-terminus protecting group or a derivative of a pharmaceutically active compound covalently bonded to the pendant functional group by means of an amide bond in the case when in the underivatized pharmaceutically active compound a carboxylic acid group is present at the position of the amide bond in the derivative.

When D is —NH—X$_1$—Z, Z is a pharmaceutically active compound covalently bonded to the pendant function group by means of X$_1$. X$_1$ is a linkage selected from

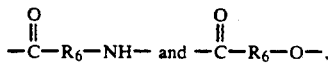

in the case when in the underivatized pharmaceutically active compound a carboxylic acid is present at the position linked to the pendant functional group by means of $X_1$; and

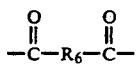

in the case when in the underivatized pharmaceutically active compound a primary or secondary amine or primary hydroxyl is present at the position linked to the pendant functional group by $X_1$. $R_6$ is the same as described above with respect to the linkages of Formula I and II.

In a third embodiment of this aspect of the invention, a polymer is provided in which a poly(alkylene oxide) having terminal amino groups and an amino acid or peptide sequence having at least one hydroxyl group are copolymerized by way of hydrolytically stable urethane linkages. The polymer contains one or more recurring structural units independently represented by Formula III, in which L is —NH— and $R_2$ is an amino acid or peptide sequence having at least one activated hydroxyl group, one carboxylic acid group when only one activated hydroxyl group is present, and at least one pendant amino group that can be further derivatized, used for crosslinking or for the attachment of ligands, like the pendant amino group of Formula IV. $R_2$ is preferably represented by Formula V:

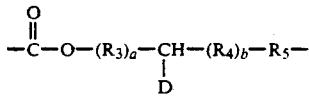

$R_3$, $R_4$, a, b and D are the same as described above with respect to Formula IV. $R_5$ is selected from:

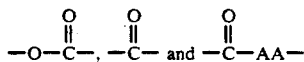

wherein —AA— is the same as described above with respect to Formula IV.

Unlike the first two embodiments of this aspect of the invention, the third embodiment does not require the amino acid or peptide sequence to have either two free amino groups or two free carboxylic acid groups. This makes available for use with the present invention natural amino acids such as hydroxylysine, serine, threonine, thyroxine and tyrosine, which can be polymerized through their hydroxyl and carboxylic acid groups, with the amino group remaining free as a pendant functional group.

In accordance with another aspect of the present invention, polymerization processes are provided for the preparation of the copolymers of the present invention. In a first embodiment of this aspect of the present invention, an interfacial polymerization process is provided for the preparation of the polymers of Formula I in which the poly(alkylene oxide) and amino acid or peptide sequence are copolymerized by means of stable urethane linkages. The process includes the steps of intimately admixing a solution of an activated poly-(alkylene oxide) in a water-immiscible organic solvent with an amino acid or peptide sequence in an aqueous solution having a pH of at least 8.0, which amino acid or peptide sequence has protected C-terminals and at least two free amino groups; and recovering from the organic solvent the resulting copolymer of the poly(alkylene oxide) and the amino acid or peptide sequence.

In accordance with a second embodiment of this aspect of the invention, a solution polymerization process is provided for the preparation of the polymers of Formula III in which the poly(alkylene oxide) and amino acid or peptide sequence are copolymerized by way of hydrolytically stable amide or hydrolyzable ester linkages. The process includes the steps of contacting a hydroxyl-terminated or amino-terminated poly-(alkylene oxide) with an amino acid or a peptide sequence in an organic solvent in the presence of coupling reagent and an acylation catalyst, which amino acid or peptide sequence has at least two free carboxylic acid groups, with the proviso that when the poly(alkylene oxide) is hydroxyl-terminated, the amino acid or peptide sequence has protected N-terminals. The resulting copolymer of the poly(alkylene oxide) with the amino acid or peptide sequence is then recovered.

In accordance with a third embodiment of this aspect of the invention, a solution polymerization process is provided for the preparation of polymers according to Formula III in which L is —NH—. A poly(alkylene oxide) having terminal amino groups is copolymerized with an amino acid or peptide sequence by way of urethane linkages formed with activated hydroxyl groups.

The process includes the step of providing an amino acid or peptide sequence having at least one hydroxyl group and protected C-terminals and activating the hydroxyl group in an organic solvent with an activating reagent in the presence of an acylation catalyst. The activated hydroxyl groups are then reacted with an amino-terminated poly(alkylene oxide) in the organic solvent and the resulting copolymer of the poly(alkylene oxide) with the amino acid or peptide sequence is then recovered. If the amino acid of peptide sequence has one hydroxyl group, the copolymer will be polymerized by way of alternating urethane and amide linkages. If the amino acid or peptide sequence has more than one hydroxyl group available for activation, polymerization can be performed exclusively through these groups by way of urethane linkages and the carboxylic acid groups of the amino acid or peptide sequence can also be protected and remain free as pendant functional groups.

In accordance with yet another aspect of the present invention, methods are provided for preparing polymer conjugates of the copolymers of the present invention and pharmaceutically active compounds. Hydrolytically stable conjugates are utilized when the pharmaceutical compound is active in conjugated form. Hydrolyzable conjugates are utilized when the pharmaceutical compound is inactive in conjugated form. The properties of the poly(alkylene oxide) dominate the copolymer and conjugate thereof.

The pharmaceutically active compound can be directly conjugated to the pendant functional group of the copolymer, or it may be conjugated by means of a bifunctional linker. The linker should contain a functional group capable of coralently bonding with the pendant functional group or a functionalized derivative thereof, and a functional group capable of covalently bonding with the pharmaceutically active compound or a functionalized derivative thereof. The linker should also contain a spacer moiety such as an aliphatic or aromatic moiety, amino acid or peptide sequence. Examples of linkers include alkanol amines, diamines, hydrazines, and the like.

As will be readily appreciated by those of ordinary skill in the art, numerous combinations of functional groups on aliphatic, aromatic, amino acid and peptide compounds exist that are capable of covalently bonding with the pendant functional groups, pharmaceutically actice compounds and functionalized derivatives thereof. However, once having the benefit of the disclosure contained in the within specification, those or ordinary skill in the art will comprehend the types of compounds suitable as being conjugate linkers.

When a linker compound is employed the order of reaction is not important. The linker may first be attached to the pendant functional group of the copolymer and then attached to the pharmaceutically active compound. Likewise, the linker may first be attached to the pharmaceutically active compound and then attached to the copolymer.

In a first embodiment of this aspect of the invention, a method is provided for preparing a polymer conjugate of a pharmaceutically active compound which compound prior to conjugation has an amino or hydroxyl group, and a copolymer of a poly(alkylene oxide) and an amino acid or peptide sequence, which amino acid or peptide sequence has, prior to conjugation, a pendant carboxylic acid group, by directly attaching the pharmaceutically active compound to the pendant functional groups of the copolymer. The method includes the steps of contacting, in an organic solvent, in the presence of an coupling reagent and an acylation catalyst, the pharmaceutically active compound and the copolymer. The resulting conjugate of the copolymer and the pharmaceutically active compound is then recovered. A hydrolytically stable amide bond is formed when the pharmaceutically active compound has an amino group prior to conjugation, linking the pharmaceutically active compound to the copolymer. When the pharmaceutically active compound has a hydroxyl group prior to conjugation, a hydrolytically unstable ester bond is formed linking the pharmaceutically active compound to the copolymer. When the pharmaceutically active compound prior to conjugation has an amino group, the copolymer can optionally have activated pendant carboxylic acid groups.

In a second embodiment of this aspect of the invention, a method is provided for preparing a polymer conjugate of a pharmaceutically active compound, which compound has a carboxylic acid group prior to conjugation, and a copolymer of a poly(alkylene oxide) and an amino acid or peptide sequence, which amino acid or peptide sequence has, prior to conjugation, a pendant carboxylic acid group or active ester thereof, using an alkanol amine linker. The method includes the steps of reacting, in an aqueous solution, in the presence of a water-soluble coupling reagent, the pendant carboxylic acid group of the copolymer with a alkanol amine, so that an alkanol amide of the carboxylic acid group is formed. The pharmaceutically active compound and the copolymer are then contacted in a suitable solvent so that an ester linkage is formed between the alkanol amide of the copolymer and the carboxylic acid group of the pharmaceutically active compound, and the resulting conjugate of the copolymer and the pharmaceutically active compound is then recovered.

In accordance with the second embodiment, the order of reaction may be reversed, so that the alkanol amine is first reacted with the carboxylic acid group of the pharmaceutically active compound to form an alkanol amide of the carboxylic acid group. The pharmaceutically active compound and the copolymer are then contacted in the organic solvent so that an ester linkage is formed between the alkanol amide of the pharmaceutically active compound and the pendant carboxylic acid group of the copolymer.

In a third embodiment of this aspect of the invention, a method is provided for preparing a polymer conjugate of a pharmaceutically active compound, which compound has a carboxylic acid group prior to conjugation, and a copolymer of a poly(alkylene oxide) and an amino acid or peptide sequence, which amino acid or peptide sequence has, prior to conjugation, a pendant carboxylic acid group or an active ester thereof, using a diamine linker. The method includes the steps of reacting, in an organic solvent, in the presence of an activating reagent and an acylation catalyst, the copolymer and a diamine, so that an amino amide of the pendant functional group is formed, and then contacting, in the organic solvent, the copolymer with the pharmaceutically active compound. The resulting conjugate of the copolymer and the pharmaceutically compound is then recovered. As with the second embodiment, the order of reaction may be reversed so that an amino amide is first formed with the carboxylic acid group of the pharmaceutically active compound, which amino amide is then reacted with the pendant carboxylic acid group of the copolymer.

Regardless of whether the amino amide is formed of the polymer pendant functional group or the pharmaceutically active compound, the pharmaceutically active compound may be reacted with an excess of copolymer, together with an additional quantity of the diamine, thereby conjugating the pharmaceutically active compound with the pendant carboxylic acid groups by way of amido amide linkages and forming available amino amide linkages with unconjugated pendant carboxylic acid groups. The available amino amide linkages of the copolymer conjugate are then further reacted, in the organic solvent, in the presence of sodium borohydride or sodium cyanoborohydride, with a monoclonal antibody having oxidized carbohydrate moieties, so that the carbohydrate moieties covalently attach to the available amino amide linkages. The resulting conjugate of the copolymer, the pharmaceutically active compound and the monoclonal antibody is then recovered.

In a fourth embodiment of this aspect of the invention, a method is provided for preparing a polymer conjugate of a pharmaceutically active compound, which compound has an aldehyde, ketone or carboxylic acid group prior to conjugation, and a copolymer of a poly(alkylene oxide) and an amino acid or peptide sequence, which amino acid or peptide sequence, prior to conjugation, has a pendant carboxylic acid group, using a hydrazine linker. The method includes the steps of reacting, in an organic solvent, in the presence of a coupling reagent and an acylation catalyst, the copolymer with an alkyl carbazate, so that an alkyl carbazate of the pendant functional group is formed, and then converting the alkyl carbazate to an acyl hydrazine. The pharmaceutically active compound is then contacted in the organic solvent with the copolymer, and the resulting conjugate of the copolymer and the pharmaceutically active compound is then recovered.

In accordance with this embodiment of the invention, the pharmaceutically active compound may be reacted with an excess of copolymer, so that fee acyl hydrazine groups remain as pendant functional groups. The method can then further include the step of reacting, in the organic solvent, in the presence of sodium borohydride, the pendant acyl hydrazine groups with a monoclonal antibody having oxidized carbohydrate moieties, so that the oxidized carbohydrate moieties form diacyl hydrazides with the pendant functional group. The resulting conjugate of the copolymer, the pharmaceutically active compound and the monoclonal antibody is then recovered.

In a fifth embodiment of this aspect of the invention, a method is provided for preparing a polymer conjugate of a pharmaceutically active compound, which compound has a carboxylic acid group prior to conjugation, and a copolymer of a poly(alkylene oxide) and an amino acid or peptide sequence, which amino acid or peptide sequence has a pendant amino group prior to conjugation, by directly attaching the pharmaceutically active compound to the pendant functional group of the copolymer. The method includes the steps of reacting, in an organic solvent, in the presence of an activating reagent and an acylation catalyst, the pharmaceutically active compound and the copolymer, and then recovering the resulting conjugate of the copolymer and the pharmaceutically active compound. In accordance with this embodiment of the invention, the pharmaceutically active compound may be reacted with an excess of the copolymer, so that pendant amino groups remain. The method then further includes the step of reacting, in the organic solvent, in the presence of sodium borohydride, the remaining pendant amino groups with a monoclonal antibody having oxidized carbohydrate moieties, so that the oxidized carbohydrate moieties covalently attach to the pendant amino groups. The resulting conjugate of the copolymer with the pharmaceutically active compound and the monoclonal antibody is then recovered.

In accordance with still yet another aspect of the present invention, a conductive composition is provided of an alkali metal electrolyte salt combined with a copolymer of a poly(alkylene oxide) and an amino acid or peptide sequence, which amino acid or peptide sequence has pendant carboxylic acid groups protected by C-terminus protecting groups. Preferably, the alkali metal electrolyte salt is a lithium salt selected from $LiAsF_6$, $LiPF_6$, $LiI$, $LiBr$, $LiBF_6$, $LiAlCl_4$, $LiCF_3CO_2$ and $LiCF_3SO_3$.

According to another aspect of the present invention, the conductive composition of the present invention is utilized as a solid electrolyte in an electrochemical cell. The electrochemical cell includes a cathode, an anode and the conductive material of the present invention. The cathode includes a cathode-active material capable of intercalating lithium and the anode is preferably a counter-electrode capable of intercalating lithium. More preferred embodiments utilize a lithiated transition metal chalcogenide as the cathode-active material and a graphitic carbon as the counter-electrode.

Still yet another aspect of the present invention provides hydrogel membranes and semi-interpenetrating polymer networks prepared from the polymers of the present invention. The hydrogel membranes have high equilibrium water content and good mechanical strength, and, as such, are suitable for many biomedical applications such as wound dressings and implants.

One embodiment of this aspect of the present invention provides hydrogel membranes of polymer matrices formed from copolymers of poly(alkylene oxides) and amino acids or peptide sequences, cross linked by way of urethane linkages between a trifunctional amine and the poly(alkylene oxide) moiety of the copolymer. The urethane linkages are non-degradable under physiological conditions. The cross link density of the membrane can be controlled by varying the length of the poly(alkylene oxide) chain used in the cross linking reaction.

A second embodiment of this aspect of the present invention provides hydrogel membranes of polymer matrices formed from copolymers of poly(alkylene oxides) and amino acids or peptide sequences, which amino acids or peptide sequences have pendant acyl hydrazine groups. The copolymers are cross linked by way of hydrolytically labile acyl semicarbazide linkages between a diisocyanate and the pendant acyl hydrazine groups of the polymer. Hydrogel membranes of this aspect of the present invention when incorporated with water, demonstrate high water content and high mechanical strength.

A third embodiment of this aspect of the present invention provides semi-interpenetrating polymer networks (IPN) of a linear, preformed second polymer entrapped within the polymer matrices of the present invention. The second polymer is chosen to be biocompatible and to improve a physical characteristic, such as tensile strength, of the polymer matrix. Polymers that are ordinarily immiscible may be combined to form the semi-IPN's of the present invention. The semi-IPN's of the present invention can be formed from polymers that would not be physically blendable by any other means. According to preferred aspects of this embodiment of the invention, the second polymer is poly(BPA carbonate) or poly(desaminotyrosyl tyrosine hexyl ester carbonate).

Still yet another aspect of the present invention provides methods by which the hydrogel membranes and semi-IPN's of the present invention may be prepared. According to one embodiment of this aspect of the present invention, a method is provided for preparing a cross linked polymer matrix of a copolymer of a poly(alkylene oxide) and an amino acid or peptide sequence, wherein at least one terminus of the copolymer is the poly(alkylene oxide). The method includes the steps of providing a first solution of the copolymer dissolved in an organic solvent in which the polymer matrix is soluble, protecting the pendant C-terminals or N-terminals of the amino acid or peptide sequence of the copolymer and then forming in the first solution an active ester of the poly(alkylene oxide) terminus of the copolymer. The first solution is then mixed with a second solution of an equivalent quantity of a trifunctional amine in a solvent in which the polymer matrix is soluble so that urethane linkages form between the active ester and the tris(amino) amine. The resulting cross-linked copolymer polymer matrix is then recovered. In accordance with this embodiment of this aspect of the present invention, a method is also provided for preparing a semi-IPN by first dissolving a linear, pre-formed second polymer in the first solution before mixing the first solution with the second solution so that the second polymer is entrapped within the cross-linked polymer matrix, as the polymer matrix is formed.

According to a second embodiment of this aspect of the present invention, a method is provided for preparing a cross-linked polymer matrix of a copolymer of a poly(alkylene oxide) and an amino acid or peptide sequence, which amino acid or peptide sequence has a pendant acyl hydrazine group. The method includes the steps of providing a solution of the copolymer in an organic solvent in which the polymer matrix is soluble and adding an equivalent quantity of diisocyanate to the solution so that acyl semicarbazide linkages form between the pendant acyl hydrazines and the diisocyanate. The resulting cross-linked copolymer polymer matrix is then recovered. In accordance with this embodiment of this aspect of the present invention, a method is also provided for preparing a semi-IPN by dissolving a linear, pre-formed second polymer in the first solution before mixing the first solution with the second solution so that the second polymer is trapped within the cross-linked copolymer matrix as the polymer matrix is formed.

It can be readily appreciated that the present invention provides a versatile family of poly(alkylene oxide) copolymers having multiple pendant functional groups at regular predetermined intervals. By being capable of forming linkages through the pendant functional groups, which linkages have varying degrees of hydrolytic stability or instability, the copolymers are useful for a variety of biomedical end-use applications.

DETAILED DESCRIPTION OF THE PREFERRED EMBODIMENT

Figure 1:
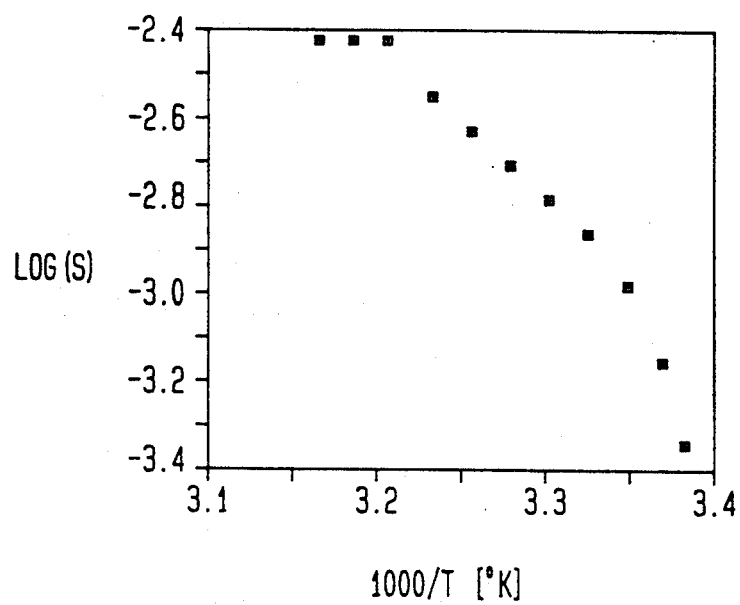
FIG. 1 depicts the weight loss with time of a hydrogel membrane of the present invention in phosphate buffer (pH 7.4) at 60° C.

The polymers of the present invention are copolymers of poly(alkylene oxides) and amino acids or peptide sequences. The polymers thus include one or more recurring structural units in which the poly(alkylene oxide) and the amino acid or peptide sequence are copolymerized by means of urethane linkages, which structural units are independently represented by Formula I disclosed above. With respect to Formula I, $R_1$ is a poly(alkylene oxide) and $R_2$ is an amino acid or peptide sequence containing two amino groups and at least one pendant carboxylic acid group.

The poly(alkylene oxides) suitable for use in the polymers of the present invention include polyethylene glycol (PEG), polypropylene glycol, poly(isopropylene glycol), polybutylene glycol, poly(isobutylene glycol) and copolymers thereof. Preferred poly(alkylene oxides) for use with the present invention have the structure:

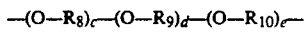

wherein $R_8$, $R_9$ and $R_{10}$ are independently selected from straight-chained and branched alkyl groups containing up to 4 carbon atoms, c is an integer between about 1 and about 100, inclusive, and d and e are independently integers between 0 and about 100, inclusive, with the proviso that the sum of c, d and e is between about 10 and about 100, inclusive.

The most preferred poly(alkylene oxide) is PEG.

The molecular weight of the poly(alkylene oxide) is not critical, and would depend mainly upon the end use of a particular copolymer. Those of ordinary skill in the art are capable of determining molecular weight ranges suitable for their end-use applications. In general, the useful range of molecular weight is a number average molecular weight between about 600 and about 200,000 daltons, and preferably between about 2,000 and about 50,000 daltons. Because the copolymers are hydrolytically stable, lower molecular weight polyalkylene oxides are preferred to insure that the resulting polymer is not too large to be eliminated by the kidney. Preferably, the molecular weight of the resulting polymer should not exceed 50,000 daltons.

The amino acid or peptide sequence represented by $R_2$ in Formula I preferably has a structure according to Formula II wherein $R_3$ and $R_4$ are independently selected from saturated and unsaturated, straightchained and branched alkyl groups containing up to 6 carbon atoms and alkylphenyl groups, the alkyl portions of which are covalently bonded to an amine and contain up to 6 carbon atoms. Included within the definition of the alkyl or phenyl portions of the alkyl phenyl groups are alkyl or phenyl groups substituted by one or more substituents selected from hydroxyl, halogens, amino, and the like. The values for a and b are independently 0 or 1. $R_5$ is —NH— or —NH—AA—, wherein —AA— is an amino acid or peptide sequence, with the proviso that —AA— contains a free N-terminus so that, when present, $R_2$ represents a peptide sequence of two or more amino acids.

The polymers of Formula I possess pendant functional groups at regular intervals within the polymer having the structure:

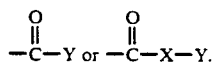

When D is

and Y is —OH, the pendant functional groups are carboxylic acid groups. The pendant carboxylic acid groups may be further functionalized, in which case Y is selected from —NH—NH$_2$, —OR$_6$—NH$_2$, —OR$_6$—OH, —NH—R$_6$—NH$_2$, —NH—R$_6$—OH, and:

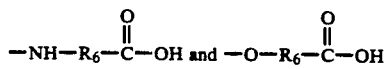

Y can also be a C-terminus protecting group or a derivative of a pharmaceutically active compound covalently bonded to the recurring structural unit by the pendant functional group. $R_6$ is selected from alkyl groups containing from 2 to 6 carbon atoms, aromatic groups alpha-, beta-, gamma- and omega amino acids, and peptide sequences.

With respect to the amino acid or peptide sequence represented by $R_2$ in Formula I and having a structure according to Formula II, $R_3$ and $R_4$ are preferably alkyl groups containing from 1 to 4 carbon atoms, inclusive. When $R_2$ is an amino acid, $R_5$ is —NH—. When $R_2$ is a peptide sequence, $R_5$ is —NH—AA—, wherein the —AA— of $R_5$ is bonded to $R_3$ or $R_4$ by way of the —NH— group of $R_5$. The single amino acids and the two or more amino acids making up the peptide sequences are preferably alpha amino acids, in which case either a or b, or both, is zero, and —AA— represents one or more alpha amino acids. Even more preferably, the amino acids and the two or more amino acids making up the peptide sequences are natural amino acids, in which instance, $R_3$ (when b is zero) or $R_4$ (when a is zero) is —CH$_2$—CH$_2$—CH$_2$— in the case of ornitine —CH$_2$—CH$_2$—CH$_2$—CH$_2$—in the case of lysine,

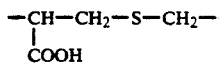

in the case of cystine, and

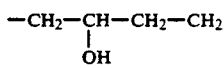

in the case of hydroxylysine, and —AA— represents one or

The peptide sequences of $R_2$ are preferably sequences containing from 2 to about 10 amino acid residues, in which case —AA— would preferably contain from 1 to about 9 amino acid residues. The peptide sequences of $R_2$ even more preferably contain from 3 to 7 amino acid residues, inclusive, in which case, —AA— would contain from 2 to 6 amino acid residues, inclusive.

As noted above, Y of the pendant functional group can be a C-terminus protecting group. C-terminus protecting groups are well-known to those of ordinary skill in the art and include those disclosed in Bodanszky, *The Practice of Peptide Synthesis* (Springer-Verlag, New York, 1984), the disclosure of which is herein incorporated by reference thereto. Preferred C-terminus protecting groups are alkyl, aryl and silicon protecting groups.

As noted above, the pendant carboxylic acid groups may be further functionalized. In such a case, Y is preferably —NH—NH$_2$. However, $R_6$, when present, is preferably an ethyl group, a natural alpha-amino acid or a peptide sequence containing from 2 to 10 natural amino acid residues.

As also disclosed above, Y can be a derivative of a pharmaceutically active compound covalently bonded to the recurring structural unit by means of the pendant functional group. Y is covalently bonded to the recurring structural unit by means of an amide bond in the case when in the underivatized pharmaceutically active compound a primary or secondary amine is present at the position of the amide bond in the derivative. Examples of underivatized pharmaceutically active compounds containing a primary or secondary amine include acyclovir, cephradine, melphalan, procaine, ephedrine, adriamycin, daunomycin, and the like.

Y is covalently bonded to the recurring structural unit by means of an ester bond in the case when in the underivatized pharmaceutically active compound a primary hydroxyl is present at the position of the ester bond in the derivative. Examples of underivatized pharmaceutically active compounds containing a primary hydroxyl group include acyclovir, plumbagin, atropine, quinine, digoxin, quinidine and the like, as well as biologically active peptides.

Y can also be a derivative of a pharmaceutically active compound covalently bonded to the recurring structural unit by means of —X—, so that the pendant functional group has the structure:

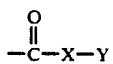

X is a linkage derived from the above-described further functionalized pendant carboxylic acid groups. X is —NH—NH— in the case when in the underivatized pharmaceutically active compound an aldehyde or ketone is present at the position linked to the pendant functional group of the recurring structural unit by means of X. Examples of underivatized pharmaceutically active compounds containing an aldehyde or ketone include adriamycin, daunomycin, testosterone, and the like. Steroids such as ketones and aldehydes are also easily generated by conventional methods.

X is —NH—NH—, —NH—$R_6$—NH—, —O—$R_6$—NH—, —O—$R_6$—O— or —NH—$R_6$—O— in the case when in the underivatized pharmaceutically active compound a carboxylic acid is present at the position linked to the pendant functional group of the recurring structural unit by means of X. Examples of underivatized pharmaceutically active compounds containing a carboxylic acid include chlorin $e_6$, cephradine, cephalothin, melphlan, penicillin V, aspirin, nicotinic acid, chemodeoxycholic acid, chlorambucil, and the like, as well as biologically active peptides.

In the case when in the underivatized pharmaceutically active compound a primary or secondary amine or primary hydroxyl is present in the position linked to the pendant functional group of the recurring structural unit by means of X, X is:

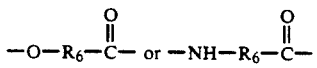

Examples of such underivatized pharmaceutically active compounds include those compounds listed above with respect to amide and ester linkages.

When X is —NH—NH—, —NH—$R_6$—NH— or —O—$R_6$—NH—, Y can also be a derivative of a monoclonal antibody having oxidized carbohydrate moieties in the case when in the underivatized oxidized monoclonal antibody a ketone or aldehyde is present at the position linked to the recurring structural unit by means of X. In this embodiment, the polymer preferably contains a recurring structural units having an oxidized monoclonal antibodies covalently bonded thereto at the pendant functional group and recurring structural units having a derivative of a pharmaceutically active compound covalently bonded thereto at the pendant functional group. The monoclonal antibody and the pharmaceutically active compound are preselected so that the monoclonal antibody targets cells for which it is specific for treatment by the pharmaceutically active compound it is co-conjugated with. For example, chlorin $e_6$ is a photosensitizer that can be co-conjugated with an anti-T cell monoclonal antibody to target the photosensitizer to T-cell leukemia cells.

Only one monoclonal antibody is required to be bound to a polymer to bind the polymer to a cell for which the monoclonal antibody is specific. The ratio of pharmaceutically active compound to monoclonal antibody should be between about 4 and about 100. Preferably, the ratio is between about 6 and about 20.

Alternatively, the polymers of the present invention can have one or more recurring structural units in which the poly(alkylene oxide) and the amino acid or peptide sequence are copolymerized by means of amide or ester linkages, which structural units are independently represented by Formula III disclosed above. With respect to Formula III, $R_1$ is a poly(alkylene oxide), L is —O— or —NH— and $R_2$ is an amino acid or peptide sequence containing two carboxylic acid groups and at least one pendant amino group. The poly(alkylene oxides) of $R_1$, and the preferred species of same, are the same as described above with respect to Formula I. However, because the amide and ester linkages are hydroslytically labile, there is no preference for limiting the molecular weight of the poly(alkylene oxide) below 50,000 daltons.

$R_2$ is preferably an amino acid or peptide sequence having a structure according to Formula IV disclosed above, wherein $R_3, R_4,$ a and b are the same as described above with respect to Formula II. $R_5$ is selected from:

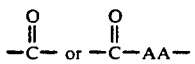

wherein —AA— is an amino acid or peptide sequences, with the proviso that —AA— contains a free C-terminus, so that when present, $R_2$ represents a peptide sequence of two or more amino acids.

The polymers of Formula III also possess pendant functional groups at regular intervals within the polymer, having the structure —NHZ or —NH—$X_1$—Z. When D is —NHZ and Z is hydrogen, the pendant functional groups are amino groups. As with the pendant carboxylic acid groups of the polymers of Formula I, the pendant amino groups may be further functionalized, in which case Z is selected from:

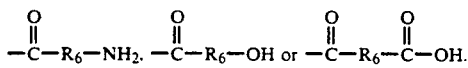

Z can also be an N-terminus protecting group or a derivative of a pharmaceutically active compound covalently bonded to the recurring structural unit by the pendant functional group. $R_6$ and the preferred species thereof are the same as described above with respect to Formula II.

With respect to the amino acid or peptide sequence represented by $R_2$ in Formula III and having a structure according to Formula IV, $R_3$ and $R_4$ are again preferably alkyl groups containing from 1 to 4 carbon atoms, inclusive. When $R_2$ is an amino acid, $R_5$ is a carboxyl group. When $R_2$ is a peptide sequence, $R_5$ is:

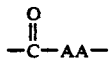

wherein the —AA— of $R_5$ is bonded to $R_3$ or $R_4$ by way of the carbonyl group of $R_5$.

The single amino acids and the two or more amino acids making up the peptide sequences are preferably alpha-amino acids, in which case a or b, or both, is zero, and —AA— represents one or more alpha-amino acids. More preferably, the single amino acids and the two or more amino acids making up the peptide sequences are natural amino acids, in which instance $R_3$ (when b is zero) or $R_4$ (when a is zero) is —$CH_2$— in the case of aspartic acid, —$CH_2$—$CH_2$— in the case of glutamic acid, and

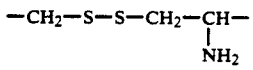

in the case of cystine.

When present, —AA— would then represent one or more natural amino acids. For —AA—, the peptide sequence lengths and preferred values therefore are the same as described above with respect to Formulas I and II.

As noted above, Z of the pendant amino group of the recurring structural unit can represent a N-terminus protecting group. N-terminus protecting groups are well-known to those of ordinary skill in the art and include those disclosed in the above-cited Bodanszky, *The Practice of Peptide Synthesis*, the disclosure of which is herein incorporated by reference thereto. The preferred N-terminus protecting groups are benzyloxycarbonyl and tert-butoxycarbonyl groups.

As also noted above, Z could also be a derivative of a pharmaceutically active compound covalently bonded to the recurring structural unit by the pendant functional group. Z is covalently bonded to the recurring structural unit by means of an amide bond in the case when in the underivatized pharmaceutically active compound a carboxylic acid group is present in the position of the amide bond in the derivative. Examples of underivatized pharmaceutically active compounds containing carboxylic acid groups include those described above for Y with respect to Formula II.

Z can also be a derivative of a pharmaceutically active compound covalently bonded to the recurring structural unit by means of —$X_1$—, so that the pendant functional group has the structure —NH—$X_1$—Z. $X_1$ is a linkage derived from the above-described further functionalized pendant amino groups. $X_1$ is a linkage selected from:

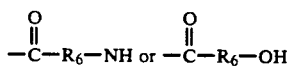

in the case when in the underivatized pharmaceutically active compound a carboxylic acid is present at the position linked to the pendant functional group of the recurring structural unit by means of $X_1$. As noted above, examples of underivatized pharmaceutically active compounds containing carboxylic acid groups have been previously listed.

In the case when in the underivatized pharmaceutically active compound a primary or secondary amine or primary hydroxyl is present at the position linked to the pendant functional group of the recurring structural unit by $X_1$, $X_1$ is:

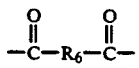

Examples of underivatized pharmaceutically active compounds containing a primary or secondary amine or primary hydroxyl are the same as those listed above for Y with respect to Formula II.

Z can also be a derivative of a monoclonal antibody having oxidized carbohydrate moieties covalently bonded to the pendant amino group of the recurring structural unit by means of an amide bond in the case when in the underivatized oxidized monoclonal antibody a ketone or aldehyde is present at the position of the amide bond in the derivative. As with the polymer having carboxylic acid pendant functional groups, the polymer having pendant amino groups preferably contains both recurring structural units having oxidized monoclonal antibodies covalently bonded thereto at the pendant functional group and recurring structural units having a derivative of a pharmaceutically active compound covalently bonded thereto at the pendant functional group, with the monoclonal antibody and the pharmaceutically active compound preselected so that the monoclonal antibody targets cells for which it is specific for treatment by the pharmaceutically active compound it is co-conjugated with.

As noted above, when L is —NH—, $R_2$ can also be an amino acid or peptide sequence having at least one activated hydroxyl group, one carboxylic acid group when only one activated hydroxyl group is present, and at least one pendant amino group. Preferably $R_2$ has the structure of Formula V, in which $R_3$, $R_4$, a, b, Z and AA and the preferred species thereof are the same as disclosed above for Formula IV and $R_5$ is selected from:

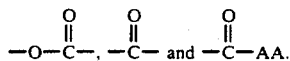

When $R_2$ is a natural amino acid, $R_3$ (when b is zero) or $R_4$ (when a is zero) is —$CH_2$— in the case of serine, and:

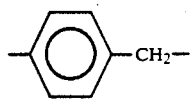

in the case of tyrosine.

The polymers of the present invention can also have both the amide and ester recurring structural units of Formula III, so that, with respect to Formula III, L is —O— for some recurring structural units and —NH— for other recurring structural units. By varying the ratio of —O— and —NH—, the hydrolytic stability of the polymer can be tailored to suit the needs of the end-use application.

The polymers of Formulas I and III have an absolute weight average molecular weight in the range of from about 10,000 to about 200,000 daltons, with about 20,000 to about 50,000 daltons being preferred for drug conjugate end-use applications. Molecular weights are determined by gel permeation chromatography relative to polyethylene glycol. Stated another way, the polymers of the present invention have from about 10 to about 100 repeating units represented by one of the structures of Formulas I and III, depending upon the molecular weight of the poly(alkylene oxide) used. As noted above, the molecular weight of the polymer should preferably not exceed 50,000 daltons, when the backbone of the polymer is not hydrolytically labile.

Interfacial Polymerization

The polymers of Formula I are prepared by an interfacial polymerization process in which the poly(alkylene oxide) and amino acid or peptide sequence are copolymerized by means of stable urethane linkages.

The interfacial polymerization utilizes a water-immiscible organic solution containing one or more activated poly(alkylene oxides). The poly(alkylene oxides) are described above and include compounds specifically enumerated as preferred. Activated poly(alkylene oxides) and the preparation of same, are well-known to those of ordinary skill in the art. For example, poly(alkylene oxides) can be activated by reaction with cyanuric chloride, or by succinylation of terminal hydroxyl groups followed by dicyclohexylcarbodiimide-mediated condensation with N-hydroxy succinimide, or by the formation of imidazolyl formate derivatives using carbonyl diimideazole, or by reaction with chloroformates of 4-nitrophenol and 2,4,5-trichlorphenol.

The preferred activated form of the poly(alkylene oxide) is the succinimidyl carbonate prepared by reacting the terminal hydroxyl groups of the poly(alkylene oxide) with phosgene to form the chloroformate, which is then reacted with N-hydroxy succinimide to form the succinimidyl carbonate. The preparation of poly(alkylene oxide) succinimidyl carbonates is described in co-pending U.S. Pat. application Ser. No. 340,928 by Zalipsky, filed Apr. 19, 1989, the disclosure of which is hereby incorporated herein by reference thereto.

The solution of the active carbonate of the poly(alkylene oxide) in the organic solvent is added to an aqueous solution containing one or more of the amino acids or peptide sequences described above, including compounds specifically enumerated as preferred, having protected C-terminals and at least two free amino groups. The aqueous solution is buffered to a pH of at least 8.0. Suitable buffers include $NaHCO_3$ and $Na_2CO_3$. The organic solution is added to the aqueous solution with vigorous stirring, which stirring is continued for several hours between about 4° C. and about 40° C. and preferably at ambient temperature. Slightly higher or lower temperatures are also suitable, depending upon the requirements of the reactants, which can be readily determined by those of ordinary skill in the art without undue experimentation. The activated poly(alkylene oxide) reacts with the amino acid or peptide sequence to produce the copolymer of Formula I. The mixture is then acidified to a pH of about 2.0 or lower. The two phases separate, with the organic phase containing the polymer.

The reaction rate is a function of the concentration of the two phases, with the reaction rate increasing as phase concentration increases. Therefore, while dilute phase concentrations are operative, higher concentrations are preferred to accelerate the reaction rate. The only upper limit to phase concentration is the solubility of the reactants in each phase. Examples of suitable water-immiscible organic solvents include methylene chloride, chloroform, dichloroethane and the like. Equimolar ratios of activated poly(alkylene oxide) to amino acid or peptide sequence starting materials are employed to maximize polymer length.

After the phases separate, the organic phase is washed with 1 N HCl followed by washing with saturated NaCl. The organic layer is then dried over anhydrous $MgSO_4$, filtered and concentrated. The polymer is precipitated using cold ether.

The polymer can then be purified by conventional purification techniques, such as by dialysis against distilled water with a molecular weight sizing membrane or by elution with a molecular weight sizing chromatography column.

Solution Polymerization—First Mode

The polymers of Formula III are prepared by a solution polymerization process in which the poly(alkylene oxide) and the amino acid or peptide sequence are copolymerized by means of hydrolytically stable amide or hydrolyzable ester linkages. The poly(alkylene oxide) should first be dried by the azeotropic removal of water by distillation in toluene, followed by drying under vacuo. The solution polymerization is carried out in an organic solvent such as methylene chloride, chloroform, dichloroethane and the like.

The poly(alkylene oxides) utilized in the reaction can have either hydroxyl terminals or amino terminals and are otherwise as described above and include compounds specifically enumerated as preferred. The poly(alkylene oxide) is dissolved in the solvent and stirred under argon. An equimolar quantity is then added of one or more of the amino acids or peptide sequences described above, including compounds specifically enumerated as preferred, having protected N-terminals. The reaction mixture may be heated slightly to dissolve the amino acid or peptide. The solution concentration of either compound is not critical. An excess quantity of a coupling reagent is also added to the reaction mixture, together with an excess quantity of an acylation catalyst. Suitable coupling reagents and the quantities to employ are well-known and disclosed by the above-cited Bodanszky, *Principles of Peptide Synthesis*, the disclosure of which is hereby incorporated herein by reference thereto.

Examples of such coupling reagents include, but are not limited to, carbodiimides such as ethyl dimethylaminopropyl carbodiimide (EDC), diisopropyl carbodiimide and 3-[2-morpholinyl-(4)-ethyl]carbodiimide, p-toluene sulfonate, 5-substituted isoxazolium salts, such as Woodward's Reagent K, and the like. Suitable acylation catalysts and the quantities to employ are also well-known, and include, but are not limited to, dimethylaminopyridinium toluene sulfonate, hydroxybenzotriazole, imidazoles, triazole, dimethyl amino pyridene, and the like.

The reaction mixture is then stirred between about 4° C. and about 40° C. and preferably at room temperature until completion of the reaction, typically within 24 hours, usually overnight.

The poly(alkylene oxide) reacts with the amino acid or peptide sequence to produce the copolymer of Formula III. A urea precipitate is removed by filtration, and the polymer is then precipitated with cold ether, filtered and dried under vacuum. The polymer can then be further purified by conventional methods, typically by reprecipitation from isopropanol.

Solution Polymerization—Second Mode

The polymers of Formula III can also be prepared by a solution polymerization process in which a poly(alkylene oxide) having amino terminals and an amino acid or peptide sequence having at least one hydroxyl group are copolymerized in an organic solvent by means of hydrolytically stable urethane linkages. The one or more hydroxyl groups of the amino acid or peptide sequence should first be activated in the organic solvent. The activation step is well-known and essentially conventional. For example, the hydroxyl group can be activated by reacting it with an alkyl chloroformate, or with p-nitrophenyl chloroformate. Alternatively, the hydroxyl group can be activated as described above with respect to the activation of poly(alkylene oxides) for the interfacial polymerization process of the present invention, preferably utilizing the process disclosed by U.S. Patent application Ser. No. 340,928 by Zalipsky, incorporated herein by reference thereto. Amino and carboxylic acid groups that are not to participate in the copolymerization, but rather are to serve as pendant functional groups, should be protected.

The activation is carried out in the presence of one or more of the activating reagents and acylation catalysts described above with respect to the first mode of solution polymerization. The same ratio of activating reagent and acylation catalyst to amino acid or peptide sequence should also be utilized. The same solvents are utilized as described above with respect to the first mode solution polymerization.

The poly(alkylene oxide) should first be dried as described above with respect to the first mode solution polymerization. After the activation of the one or more hydroxyl groups of the amino acid or peptide sequence is complete, the poly(alkylene oxide) is then added to the reaction mixture with stirring. As with the first mode solution polymerization equimolar quantities of reactants are preferred. The reaction mixture is then stirred at room temperature until completion of the reaction, typically within 24 hours, usually overnight.

The poly(alkylene oxides) utilized in the reaction have amino terminals and are otherwise as described above and include compounds specifically enumerated as preferred. The poly(alkylene oxide) reacts with the activated hydroxyl groups of the amino acid or peptide sequence to form urethane linkages. When the amino acid or peptide sequence contains only one hydroxyl group to be activated, a carboxylic acid group is also left unprotected and the poly(alkylene oxide) reacts with this carboxylic acid group as in the first mode solution polymerization to form an amide linkage.

The resulting polymer is then precipitated, separated and purified as described above with respect to the first mode solution polymerization.

The polymers of the present invention can be used in the preparation of drug carriers by conjugating the pendant functional groups either directly with reactive functional groups on a drug molecule, or by first further functionalizing the pendant functional group to improve its reactivity with or selectivity for a functional group on a candidate drug molecule. Accordingly, the copolymers of the present invention can be conjugated with candidate drug molecules by one of the modes of conjugation set forth below.

Drug Conjugation—First Mode

The polymers of Formula I, having pendant carboxylic acid groups, can be directly conjugated with pharmaceutically active compounds that, prior to conjugation, have an amino or hydroxyl group. The polymers of Formula I are described above, and include polymers specifically enumerated as preferred. Pharmaceutically active compounds having amino or hydroxyl groups are also described above.

The conjugation reaction utilizes an organic solvent in which the reactants are soluble. Examples of suitable organic solvents include DMF, $CH_3CN$, $CH_2Cl_2$, and the like. The appropriate quantities of the polymer and the pharmaceutically active compound are dissolved in the solvent. The solvent may be heated slightly to dissolve the reactants. An excess of the pharmaceutically active compound is preferred to insure substantial conjugation of the pendant functional groups of the polymers. The total solution concentration (w/v%) of both compounds combined is not critical, and will vary depending upon the solubility of the materials. Complete solubility of the pharmaceutically active compound is also not critical, because the compound will be solubilized upon conjugation with the polymer. An activating reagent and an acylation catalyst are also added to facilitate the reaction as described above with respect to the interfacial polymerization.

The reaction mixture is then stirred between about 4° C. and about 40° C. until completion of the reaction, typically within 24 hours, usually overnight. Temperatures between about 15° C. and about 25° C. are more preferred and temperatures close to or below room temperature are even more preferred to preserve the integrity of the biologically active molecule and to minimize side reactions.

A urea product precipitates, which is removed by filtration. The polymer conjugate is then precipitated with a solvent in which the polymer has poor solubility, e.g., ether, hexane and the like, filtered and purified by further reprecipitation crystalization, from such solvent as ethanol, ethyl acetate, iso-propanol and the like. The product then is dried in vacuo.

As noted above, when the pharmaceutically active compound has a hydroxyl group prior to conjugation, a hydrolytically unstable ester bond is formed linking the pharmaceutically active compound to the copolymer by means of the pendant functional group. When the pharmaceutically active compound has an amino group prior to conjugation, a hydrolytically stable amide bond is formed linking the pharmaceutically active compound to the copolymer by means of the pendant functional group. If the pharmaceutical compound is active in conjugated form, then a hydrolytically stable bond is desirable. However, if the pharmaceutical compound is inactive in conjugated form, then a hydrolytically unstable bond is desirable. When the pharmaceutically active compound has both an amino and a hydroxyl group, the question of which group to conjugate to will thus depend upon the activity of the pharmaceutical compound in conjugated form. Once a decision is made to conjugate to either the amino group or the hydroxyl group, the group through which conjugation is not to occur should be protected to prevent the formation of undesirable conjugates. The attachment of such protective groups is well-known to those of ordinary skill in the art.

When the pharmaceutically active compound prior to conjugation has an amino group, the pendant carboxylic acid group at the copolymer is preferably an activated pendant carboxylic acid group. The activation of such carboxylic acid groups is well-known and essentially conventional. For example, the pendant carboxylic acid group can be reacted with N-hydroxy succinimide in the presence of a coupling agent such as dicyclohexyl carbodiimide in a solvent such as DMF, $CHCl_3$, pyridine and the like.

Drug Conjugation—Second Mode

The polymers of Formula I having pendant carboxylic acid groups can also be conjugated with pharmaceutically active compounds that, prior to conjugation, have a carboxylic acid group, by first reacting the pendant carboxylic acid group of the copolymer with a alkanol amine, so that an amide of the pendant carboxylic acid group is formed. The polymers of Formula I are disclosed above and include polymers specifically enumerated as preferred. Pharmaceutically active compounds having a carboxylic acid group are also described above.

Pharmaceutically active compounds having a carboxylic acid group can also be formed from pharmaceutically active compounds having hydroxyl groups by forming an acid ester of the hydroxyl group with a dicarboxylic acid anhydride, such as succinic anhydride, or an N-dicarboximide, such as N-hydroxy succinimide. For example, the hydroxyl group of the pharmaceutically active compound can be reacted with succinic anhydride in the presence of a base such as triethylamine in a suitable solvent such as DMF. Pharmaceutically active compounds having a hydroxyl group are described above. Alkanol amines are defined as including, in addition to compounds such as ethanol amine or 3-propanol amine, amino acids and peptide sequences having free hydroxyl and amino groups, so that alkanol amines suitable for use in the present invention have the structure $HO-R_6-NH_2$, wherein $R_6$ and the preferred species thereof are the same as described above with respect to Formula II.

The reaction between the copolymer and the alkanol can be performed in aqueous solution. The polymer is dissolved in the solution with an excess, preferably at least a ten-fold excess of a alkanol amine. The pH of the solution is then adjusted to between about 4.5 and about 6 by the addition of 0.1 N HCl. At least a ten-fold excess of a water-soluble coupling reagent is then added with maintenance of the pH within the above range by the addition of 1 N HCl. The reaction mixture should be stirred, for about 5 to about 48 hours, acidified, and extracted into an organic solvent such as methylene chloride, $CHCl_3$ dichloroethane, and the like. The solvent extract is then washed with 1 N HCl followed by washing with saturated NaCl. The extract is then dried over anhydrous $MgSO_4$, filtered and concentrated to a viscous syrup. The polymer product is then precipitated using cold ether. The polymer product can then be purified by reprecipitation from isopropanol, followed by washings with hexane and complete drying in vacuo.

Suitable water-soluble coupling reagents are well-known and disclosed by the above-cited Bodanszky, *Principles of Peptides Synthesis*, the disclosure of which is hereby incorporated herein by reference thereto. The examples of such coupling reagents include, but are not limited to, water-soluble carbodiimides such as EDC, and 3-[morpholinyl-(4)-ethyl]carbodiimide, p-toluene sulfonate, 5-substituted isoxazolium salts, such as Woodward's Reagent K, and the like.

The alkanol amide of the copolymer is then reacted with the carboxylic acid group of the pharmaceutically active compound in a solvent such as DMF, $CH_2Cl_2$, pyridine, and the like. The appropriate quantities of the hydroxyl amide the polymer and the pharmaceutically active compound are combined in the solvent, which may be heated slightly to dissolve the reactants Again, excess quantities of the pharmaceutically active compound are preferably employed to insure substantial conjugation of the pendant hydroxyl amides of the polymer.

The reaction is carried out in the presence of one or more of the coupling reagents and acylation catalysts described above with respect to the first mode of drug conjugation. The amount of coupling reagent and acylation catalyst should be equivalent to or in excess of the amount of pharmaceutically active compound.

The carboxylic acid group of the pharmaceutically active compound is preferably an activated carboxylic acid group. The carboxylic acid group of the pharmaceutically active compound can be activated by the method described above for activation of the pendant carboxylic acid group of the polymer. Other activating methods are well known and essential conventional.

The reaction mixture is then stirred at between about 4 and about 40° C., and preferably about room temperature, until completion of the reaction, typically within 24 hours, usually overnight.

The hydroxyl group of the pendant alkanol amide then reacts with the carboxylic acid group of the pharmaceutically active compound to form an ester linkage. A urea product precipitates that is removed by filtration. The product is then precipitated, filtered, dried and purified according to the procedure described above with respect to the first mode of drug conjugation.

The above order of reaction may be reversed, so that the alkanol amine is first reacted with a pharmaceutically active compound having a carboxylic acid group, which carboxylic acid group may be optionally activated, to form a alkanol amide thereof. Suitable optional activating steps are well-known and essentially conventional. For example, the carboxylic acid group of the pharmaceutically active compound can be reacted with an alkyl or p-nitrophenyl chloroformate in the presence of a base such as triethyl amine in a suitable solvent such as DMF. The pharmaceutically active compound with the activated carboxylic acid group is then precipitated, dried and purified by conventional means and reacted with the alkanol amine by the process described above for the copolymer.

The resulting alkanol amide of the pharmaceutically active compound is then reacted with the carboxylic acid group of the copolymer, following the procedure described above so that an ester linkage forms between the alkanol amide of the pharmaceutically active compound and the pendant carboxylic acid group of the copolymer, following the procedure described above for the formation of the ester linkage between the alkanol amide of the copolymer and the carboxylic acid group of the pharmaceutically active compound. The pendant carboxylic acid group of the copolymer is preferably activated in accordance with the optional procedures set forth for this mode when the alkanol amide of the pendant carboxylic acid group of the copolymer is first formed.

As with the first mode of drug conjugation, the pendant carboxylic acid groups of the copolymer are preferably activated pendant carboxylic acid groups, which carboxylic acid groups can be activated in the manner described above with respect to the first mode of drug conjugation.

Drug Conjugation—Third Mode

The polymers of Formula I, having pendant carboxylic acid groups, can also be directly conjugated with pharmaceutically active compounds having, prior to conjugation, carboxylic acid groups, by first reacting the pendant carboxylic acid groups of the polymer with a diamine, so that an amino amide of the pendant carboxylic acid group is formed. The amino amide is then reacted with the carboxylic acid group of the pharmaceutically active compound to form an amido amide linkage between the pendant carboxylic acid group of the copolymer and the carboxylic acid group of the pharmaceutically active compound. The polymers of Formula I are described above and include polymers specifically enumerated as preferred. Pharmaceutically active compounds having a carboxylic acid group are also described above.

Pharmaceutically active compounds having a carboxylic acid group can also be formed from pharmaceutically active compounds having hydroxyl groups by forming an acid ester of the hydroxyl group as described above with respect to the second mode of drug conjugation. Pharmaceutically active compounds having a hydroxyl group are also described above. Diamines are defined as including, in addition to compounds such as ethylene diamine, amino acids and peptide sequences having two free amino groups, so that diamines suitable for use with the present invention have the structure $H_2N-R_6-NH_2$, wherein $R_6$ and the preferred species thereof are the same as described above with respect to Formula II.

The reaction between the copolymer and the diamine utilizes an aqueous solution. The polymer is dissolved in the solution with an excess, preferably at least a ten-fold excess of the diamine, which excess is utilized in order to minimize undesirable cross linking reactions. The pendant carboxylic acid groups of the copolymer are preferably activated pendant carboxylic acid groups, which pendant carboxylic acid groups are activated as described above with respect to the second mode of drug conjugation.

The diamine is reacted with the pendant carboxylic acid group of the copolymer by the same method described above with respect to the second mode reaction between the alkanol amine and the pendant carboxylic acid group of the copolymer. The reaction mixture is made basic and extracted with an organic solvent such as methylene chloride. The solvent extract is washed, dried, filtered, concentrated, precipitated and purified by the procedure described above with respect to the alkanol amide of the copolymer prepared pursuant to the second mode of drug conjugation.

The pendant amino amide of the copolymer is then reacted with the carboxylic acid group of the pharmaceutically active compound as described above with respect to the second mode of drug conjugation.

The carboxylic acid group of the pharmaceutically active compound is preferably an activated carboxylic acid group. The carboxylic acid group can be activated by the conventional means mentioned above with respect to the second mode of drug conjugation for the reaction of the amine portion of the alkanol amine with the carboxylic acid group of the pharmaceutically active compound.

The reaction mixture is then stirred under the conditions described above with respect to the first mode of drug conjugation. The pendant amino amide then reacts with the carboxylic acid group of the pharmaceutically active compound to form an amide linkage. The work up and isolation of the polymer product is the same as described above with respect to the first mode of drug conjugation.

The above order of reaction may be reversed so that the diamine is first reacted with a pharmaceutically active compound having a carboxylic acid group following the procedure described above for the reaction of the amino amide of the copolymer with the carboxylic acid group of the pharmaceutically active compound. The reaction forms an amino amide of the carboxylic acid group of the pharmaceutically active compound. The carboxylic group of the pharmaceutically active compound is preferably an activated carboxylic acid group, which may be activated by conventional means, such as by reaction with a carbodiimide.

The resulting amino amide of the carboxylic acid group of the pharmaceutically active compound is then reacted with the pendant carboxylic acid group of the copolymer following the procedure described above for the reaction of the diamide with the pendant carboxylic acid group of the copolymer. An amide linkage is formed between the amino amide and the pendant carboxylic acid group. The pendant carboxylic acid group is preferably an activated carboxylic acid group, prepared as described above with respect to the first mode of drug conjugation.

Drug Conjugation—Fourth Mode

The polymers of Formula I, having pendant carboxylic acid groups, can also be conjugated with pharmaceutically active compounds that, prior to conjugation, have an aldehyde, ketone or carboxylic acid group. The fourth mode of drug conjugation first forms pendant acyl hydrazine groups from the pendant carboxylic acid groups of the polymer, which acyl hydrazine is then reacted with the aldehyde, ketone or carboxylic acid group of the pharmaceutically active compound to form a hydrazone or diacyl hydrazide linkage between the copolymer and the pharmaceutically active compound. The polymers of Formula I are described above and include polymers specifically enumerated as preferred. Pharmaceutically active compounds having an aldehyde, ketone or carboxylic acid group are also described above.

Pharmaceutically active compounds having a carboxylic acid group can also be formed from pharmaceutically active compounds having hydroxyl groups by forming an acid ester of the hydroxyl group as described above with respect to the second mode of drug conjugation. Pharmaceutically active compounds having a hydroxyl group are also described above.

The fourth mode of drug conjugation first forms pendant acyl hydrazine groups on the polymer by reacting the pendant carboxylic acid groups of the polymer with an alkyl carbazate, so that the pendant carboxylic acid groups form pendant alkyl carbazate groups. The alkyl portion is acting as a protecting group. It is removed in the subsequent step to yield acyl hydrazine. The reaction utilizes an organic solvent such as methanol in which the polymer and an excess, preferably at least a ten-fold excess of an alkyl carbazate are reacted at between about 4° C. and about 40° C. in the presence of an excess quantity of a coupling reagent. The most preferred alkyl carbazate is t-butyl carbazate. Examples of suitable coupling reagents include those listed above with respect to the first mode of drug conjugation. Likewise, the work-up and isolation of the polymer product is the same as described above with respect to the first mode of drug conjugation.

The alkyl carbazate group is then removed to form pendant acyl hydrazine groups by mixing the polymer with a 4 M solution of HCl in dioxane. The mixture is stirred for between about 30 min. and about 2 hours at room temperature, with the polymer settling at the bottom as an oil. The hydrochloride salt of the hydrazine is then worked-up and isolated as described above.

The polymer having pendant acyl hydrazine groups is then conjugated with the pharmaceutically active compound. The conjugation reaction utilizes an organic solvent in which the reactants are soluble. Examples of suitable organic solvents include pyridine, DMF, $CH_2Cl_2$, THF, and the like. The polymer having pendant acyl hydrazine groups and the pharmaceutically active compound are dissolved in the solvent and reacted as disclosed above with respect to the first mode of drug conjugation.

The pendent acyl hydrazine groups of the polymer react with the aldehyde and ketone to form a hydrazaone or with the carboxylic acid group of the pharmaceutically active compound to form a diacyl hydrazide linkage. Hydrazaones can be formed with aldehyde or ketone containing drugs (adriamycine, testosterone) or when aldehydes or ketones are introduced (e.g., by oxidation of carbohydrate residues of glycopeptides such as disclosed by the co-pending U.S. Pat. application Ser. No. 673,696 by Zalipsky et als, filed Mar. 15, 1991, the disclosure of which is hereby incorporated herein by reference thereto). The work-up and isolation of the polymer product is the same as described above with respect to the first mode of drug conjugation.

When the pharmaceutically active compound has a carboxylic acid group, the carboxylic acid group is preferably an activated carboxylic acid group, substituted with a suitable leaving group capable of being displaced by the pendant acyl hydrazine group of the polymer. Examples of suitable leaving groups are disclosed by Bodanszky, *Principals of Peptide Synthesis*, cited above, the disclosure of which is hereby incorporated herein by reference thereto. Such leaving groups, which are well-known, include, but are not limited to, imidazolyl, triazolyl, N-hydroxy succinimidyl, N-hydroxy norbornene dicarboximidyl and phenolic leaving groups, and are substituted onto the carboxylic acid group of the pharmaceutically active compound by reacting the carboxylic acid group in the presence of an activating reagent with the corresponding imidazole, triazole, N-hydroxy succinimide, N-hydroxy norbornene dicarboximide and phenolic compounds. Suitable activating reagents include those disclosed above with respect to the first mode of drug conjugation.

Drug Conjugation—Fifth Mode

The polymers of Formula III having pendant amino groups can be directly conjugated with pharmaceutically active compounds that, prior to conjugation, have a carboxylic acid group. The polymers of Formula III are described above, and include polymers specifically enumerated as preferred. Pharmaceutically active compounds having carboxylic acid groups are also described above. Pharmaceutically active compounds having a carboxylic acid group can also be formed from pharmaceutically active compounds having hydroxyl groups by reacting the hydroxyl group as described above with respect to the second mode of drug conjugation. Pharmaceutically active compounds having a hydroxyl group are described above.

The polymer and the pharmaceutically active compound are reacted and recovered as described above in the fourth mode of drug conjugation for the reaction between the polymer having pendant acyl hydrazine groups and the pharmaceutically active compound having carboxylic acid groups. The pendant amino group of the polymer reacts with the carboxylic acid group of the pharmaceutically active compound to form an amide linkage.

The carboxylic acid group of the pharmaceutically active compound is preferably an activated carboxylic acid group, substituted with a suitable leaving group capable of being displaced by the pendant amino group of the polymer. The activation of such carboxylic acid groups is well-known and essentially conventional. The carboxylic acid groups of the pharmaceutically active compounds can be activated as described above with respect to the fourth mode of drug conjugation.

The polymers of Formulas I and III can also be conjugated with biologically active polypeptides and glycopolypeptides. Biologically active polypeptides and glycopolypeptides of interest include those listed in the above-incorporated copending U.S. Pat. application Ser. No. 673,696 by Zalipsky et als. The biologically active polypeptides and glycopolypeptides contain aldehyde, ketone and carboxylic acid groups that can be conjugated with the polymers of the present invention according to the third, fourth and fifth modes of drug conjugation, or according to the methods described in the above-incorporated U.S. Pat. application Ser. No. 673,696 by Zalipsky et als.

Targeted Immunotherapy

Another class of biologically active glycopolypeptides of interest are monoclonal antibodies. Monoclonal antibodies contain carbohydrate moieties capable of being oxidized to form aldehydes and ketones. The groups can be generated on the carbohydrate moieties, for example, by oxidizing the vicinal diols of the carbohydrate moieties with excess periodate, or enzymatically, e.g. by use of galactose oxidase, using the methods described in the above-incorporated U.S. Pat. application Ser. No. 673,696 by Zalipsky et als.

Clearly, the ketones and aldehydes of the oxidized carbohydrate moieties of monoclonal antibodies can be coupled with the polymers of Formula I by the fourth mode of drug conjugation disclosed above. Sodium borohydride or sodium cyanoborohydrate is added to the reaction mixture to reduce the resulting hydrazone to a more stable alkyl hydrazide.

However, the oxidized carbohydrate moieties of monoclonal antibodies will also react with amino amides formed from pendant carboxylic acid groups of the polymers of Formula I, according to the third mode of drug conjugation, as well as with the pendant amino groups of the polymers of Formula III, according to the fifth mode of drug conjugation, in the presence of sodium borohydride. The attachment of a single monoclonal antibody to a polymer is sufficient to bind the polymers to cells for which the monoclonal antibody is specific.

When a polymer according to Formula I or Formula III has monoclonal antibodies conjugated thereto, the polymer can be co-conjugated with a pharmaceutically active compound to deliver the compound to the specific cell the monoclonal antibodies function to bind the polymer to. Specific cells can be targeted for treatment by the pharmaceutically active compound, significant quantities of which will not be delivered to other tissues. This is particularly important in applications when the pharmaceutically active compound produces toxic or other undesirable side effects in tissues not intended for treatment. Lower dosage quantities will also be possible because application of the pharmaceutically active compound will be essentially limited to the treatment site. For example, chemotherapeutic compounds can be used to treat cancerous cells that would otherwise be toxic to healthy tissues.

The co-conjugates of pharmaceutically active compounds and monoclonal antibodies with the polymers of Formulas I and III are formed by first reacting the pharmaceutically active compound with the polymer according to either the third, fourth or fifth mode of drug conjugation. An excess of polymer is utilized so that pendant functional groups will remain unconjugated for the attachment of the monoclonal antibody. The carbohydrate moieties of the monoclonal antibody are first oxidized to produce aldehyde and ketone groups for conjugation, and the monoclonal antibody is then reacted with the conjugate of the pharmaceutically active compound and the copolymer of Formula I or III having available pendant functional groups according to the third, fourth or fifth mode of drug conjugation, as if the monoclonal antibody were a pharmaceutically active compound. As noted above, the reaction can be performed in the presence of sodium borohydride or sodium cyanoborohydrate to convert the resulting hydrazone to a hydrazide. The co-conjugates of the pharmaceutically active compound and monoclonal antibody with the polymer of Formula I or III can then be purified by protein chromatography by conventional methods.

A number of useful combinations of pharmaceutically active compounds and monoclonal antibodies are available for the treatment of specific cell types in need thereof with suitable pharmaceutically active compounds. For example, as described above, chlorin $e_6$, a photosensitizer, can be co-conjugated with an anti-T cell monoclonal antibody to bind the polymer-drug conjugation to T-cell leukemia cells. Thus, only the T-cells are rendered photosensitive and subsequent treatment with ultraviolet light substantially reduces or eliminates the T-cell leukemia cells without affecting other types of cells.

Other pharmaceutically active compounds preferably co-conjugated with monoclonal antibodies include cytotoxic drugs such as daunomycin, metotrexate, cytorhodin-S, adriamycin, mitomycin, doxorubicin, melphalan and the like. Metal chelating compounds such as EDTA can be co-conjugated with monoclonal antibodies to form complexes with radioative isotpes for the treatment of cells in need thereof, to which the monoclonal antibody is capable of binding. Examples of radioactive isotopes include, but are not limited to $99_{Tc}$ and $123_I$, which can be used, for example in the treatment of cancerous cells.

A large number of pharmaceutically active compounds may be conjugated with the polymers of Formulas I and III, including antibiotics, anti-neoplastic agents, antiviral agents, cytotoxic drugs, metal chelators, hormones, and the like. The resulting conjugate can be prepared for administration by incorporating the same into a suitable pharmaceutical formulation.

Examples of suitable pharmaceutical formulations are well-known in the art and may include, but are not limited to, phosphate buffered saline solutions, water, emulsions such as oil/water emulsion, and various types of wetting agents. Other suitable pharmaceutical formulations include sterile solutions, tablets, coated tablets and capsules.

Typically, such pharmaceutic formulations contain excipients such as starch, milk, sugar, certain types of clay, gelatin, stearic acid or salts thereof, such as magnesium or calcium stearate, talc, vegetable fats or oils, gums, glycols, and the like. Such formulations may also include flavor and color additives or other ingredients.

Compositions of such formulations are prepared by well-known conventional methods.

The invention also provides a method for treating a pathological condition in a subject in need thereof by administering to the subject the composition of the present invention. Administration of the medication may occur in one of several ways, including oral, intravenous, intraperitoneal, subcutaneous, intramuscular, topical or intradermal administration.

Ionically Conductive Materials

Certain of the polymers of Formula I form an ionically conductive material when combined with an alkali metal electrolyte salt. The polymers of Formula I are described above, and include polymers specifically enumerated as preferred. The polymers of Formula I capable of forming ionically conductive materials are those polymers in which Y is —OH or a C-terminus protecting group having the structure —OR$_7$, wherein R$_7$ is an alkyl group and preferably an ethyl group.

The alkali metal electrolyte salt is preferably a lithium electrolyte salt. Suitable lithium salts include LiAsF$_6$, LiPF$_6$, LiI, LiBr, LiBF$_6$, LiAlCl$_4$, LiCF$_3$CO$_2$, LiCF$_3$SO$_3$. Preferred lithium electrolyte salts include LiAsF$_6$, LiPF$_6$, LiI and LiCF$_3$SO$_3$. The most preferred lithium electrolyte salts are LiAsF$_6$ and LiCF$_3$SO$_3$.

The preparation of the ionically conductive materials utilizes an organic solvent in which the polymer and the alkali metal electrolyte salt are soluble, such as acetonitrile. The ratio of polymer to electrolyte salt should be between about 2:1 and about 10:1 and preferably about 4:1. The total solution concentration (w/v%) of both compounds combined is between about 1 percent and about 25 percent, and preferably about 10 percent, depending upon the solubility of the materials. The polymer and electrolyte salt are dissolved in the solvent, which may be heated slightly to dissolve the materials. The mixture is cast into the desired form, and the solvent is removed by drying, first in air and then under vacuum. The mixture may be heated to remove the solvent.

The polymers preferably have a molecular weight greater than about 75,000 daltons to provide the mixture with adequate mechanical strength. The polymers are also preferably cross-linked, as set forth below, to provide adequate mechanical strengths to the material. The mixture of polymer and electrolyte salt with solvent removed may also be compression molded to obtain articles having a desired form.

The ionically conductive materials of the present invention are useful as electrodes in electrochemical cells. However, the ionically conductive materials of the present invention, instead of being utilized as electrodes, are particularly useful as solid electrolytes for non-aqueous electrochemical cells. The mixture is particularly well suited for use in non-aqueous secondary cells.

Non-aqueous electrochemical cells can be assembled utilizing the ionically conductive material of the present invention by combining a cathode, an anode and a solid electrolyte containing the ionically conductive material. Examples of suitable anodes include alkali metals such as sodium, potassium and lithium. The alkali metal electrolyte salt would then be a salt of the metal utilized. The preferred alkali metal is lithium.

The anode can also be a counter-electrode capable of reversibly intercalating lithium from the cathode. In this instance, then, the alkali metal electrolyte salt must be a lithium salt. Anodes that function as counter-electrodes capable of reversibly intercalating lithium are well-known and are prepared from graphitic carbon.

The cathode preferably contains a cathode-active material capable of reversibly intercalating lithium. Suitable lithium-intercalable cathode materials include metal-chalcogen combinations, particularly transition metal-chalcogen combinations, metal halides, and the like. Chalcogens are understood by those of ordinary skill in the art to include the chemically-related elements from Group VI of the periodic table, namely oxygen, sulfur, selenium, tellurium and polonium. The preferred chalcogens are oxygen and sulfur. Preferred transition metals include manganese, nickel, iron, chromium, titanium, vanadium, molybdenum and cobalt. Preferred compositions include molybdenum sulfides, vanadium oxides and manganese oxides. MoS$_2$, V$_6$O$_{13}$, Mo$_6$S$_8$ and MnO$_2$ are more preferred, with MnO$_2$ being most preferred.

It is desirable that the cathode, as well as the anode, when carbonaceous materials are utilized, maintain their electrical conductivity at all states of charge. Conductivity may be enhanced by utilizing the ionically conductive materials of the present invention as a binder for the cathode-active materials and for the carbonaceous counter-electrodes of the anode.

In assembling the cells of the present invention, the cathode is typically fabricated by depositing a slurry of a cathode-active material, ionically conductive binder and a fugitive liquid carrier such as one of the solvents utilized in the preparation of the ionically conductive materials, on a cathode current collector, and then evaporating the carrier to leave a coherent mass in electrical contact with the current collector. Likewise, the anode may be prepared by depositing a slurry of a carbonaceous anode material, the ionically conductive binder and the fugitive liquid carrier on an electrically-conductive anode support and then evaporating the carrier to leave a coherent mass in electrical contact with the anode support. The cell is then assembled by sandwiching the cathode and anode layers with the solid electrolyte containing the ionically conductive material of the present invention layered therebetween. The anode and cathode current collectors are then placed in electrical contact with their respective anode and cathode terminals. The ionically conductive binder may be present in an amount between about 0.5 percent and about 25 percent by weight of the cathode or anode material, and preferably between about 2 percent and about 10 percent by weight.

Cross-Linked Polymer Products

The polymers of Formulas I and III can also be cross-linked to form polymer matrices that can be utilized in the preparation of hydrogel membranes and semi-interpenetrating polymer networks (semi-IPN's). The polymers of Formulas I and III can be cross-linked by way of hydrolytically stable urethane linkages between a trifunctional amine and the poly(alkylene oxide) moiety of the copolymer. The polymers of Formula I, having pendant acyl hydrazine groups, can also be cross-linked by way of hydrolytically labile acyl semicarbazide linkages between a diisocyanate and the pendant acyl hydrazine groups of the polymer. The cross-link density of the polymer matrix can be controlled by varying the length of the poly(alkylene oxide) moiety of the polymers of Formulas I and III. The polymers of Formulas I and III are described above and include polymers specifically enumerated as preferred. The polymer matrices cross-linked by way of acyl semicarbazide linkages utilize polymers according to Formula I having pendant acyl hydrazine functional groups that are prepared as described above with respect to the fourth mode of drug conjugation.

As noted above, the cross-linking reaction to form urethane linkages reacts a trifunctional amine with the poly(alkylene oxide) moiety of the copolymer. Accordingly, polymers having terminal poly(alkylene oxide) groups should be used. Such polymers can be obtained from the polymerization processes of the present invention by reacting the amino acids or peptide sequences with an excess of poly(alkylene oxide).

The terminal poly(alkylene oxide) groups should be activated poly(alkylene oxide) groups. The polymers of Formula I produced by the interfacial polymerization process described above will have activated terminal poly(alkylene oxide) groups. The polymers of Formula III are prepared by the solution polymerization processes described above, which do not result in polymers having activated terminal poly(alkylene oxide) groups. However, the terminal poly(alkylene oxide) groups of the polymers of Formula III can be activated by the methods described above with respect to the interfacial polymerization process for the preparation of the polymers of Formula I. However, the activation step should not be performed until after the polymerization of the polymers of Formula III.

The urethane cross-linking reaction utilizes an solvent in which the reactants are soluble. Examples of suitable solvents include methylene chloride, chloroform, THF, dioxane, water, DMF, acetonirile, and the like. Equivalent quantities of the polymer and the trifunctional amine are reacted. Trifunctional amines are defined as any compound having three free amine groups, including aromatic materials. Suitable trifunctional amines include any soluble material having three amines that can be used as a cross-linking agent. preferred trifunctional amines have the structure $N(-R_6-NH_2)_3$, in which $R_6$ is the same as described above with respect to Formula II. Trifunctional amines, the alkyl moieties of which have between about 1 and about 10 carbon atoms are preferred. Trifunctional amines with alkyl moieties having between about 2 and about 6 carbon atoms are even more preferred.

Separate solutions of the polymer and the trifunctional amine are prepared. The solvents may be heated slightly to dissolve the reactants. The solution concentration (w/v%) of the polymer solution should be less than about 10 percent so that cross-linking of the polymer does not occur too rapidly.

The solution of the amine is added to the polymer solution with stirring. Within minutes the mixture is poured into molds, with the solvent permitted to slowly evaporate. The evaporation is usually complete within 24 hours, typically overnight. The cross-linked polymer matrix forms a film that can be peeled from the mold. N-hydroxy succinimide is a bi-product of the cross-linking reaction and will remain embedded in the polymer matrix unless removed by washing with water. However, this is readily accomplished by rinsing the membrane with several successive washings of distilled, deionized water. Analysis of the washing has shown that substantially all of the N-hydroxy succinimide is removed by the first washing.

Polymer matrices cross-linked by urethane linkages can also be prepared utilizing the poly(alkylene oxide) homopolymers disclosed above as starting materials for the interfacial polymerization process described above. In other words, it is not necessary for this cross-linking method that the poly(alkylene oxide) be copolymerized with an amino acid or peptide sequence.

The acyl semicarbazide cross-linking of the polymers of Formulas I having pendant acyl hydrazine groups does not require the use of polymers having terminal alkylene oxide moieties. The reaction utilizes the same organic solvents utilized in the urethane cross-linking reaction. Equivalent quantities of the polymer and the diisocyanate are reacted. Suitable diisocyanates have the structure $O=C=N-R_6-N=C=O$, in which $R_6$ is the same as described above with respect to Formula II. Alkyl diisocyanates, the alkyl moieties of which have between 1 and about 10 carbon atoms are preferred. Alkyl diisocyanates with alkyl moieties having between about 2 and about 6 carbon atoms are even more preferred. Aromatic diisocyanaters such as toluene diisocyanate are also suitable for use with the present invention. The solution concentration (w/v%) of the polymer should again be less than 10 percent so that cross-linking does not occur too rapidly.

The polymer is dissolved first and the solvent may be heated slightly to dissolve the material. To this solution is added an excess of a base such as triethylamine or sodium bicarbonate to convert the hydrochloride of the pendant hydrazine groups to the free base. Once the conversion is complete, the solution is filtered and the residue washed with the reaction solvent. The alkyl diisocyanate is added to the combined filtrate with stirring. Within minutes the solution is poured into molds, with the solvent permitted to slowly evaporate. Evaporation is usually complete within 24 hours, typically overnight. The cross-linked polymer matrix forms a film that can be peeled from the mold.

The above-disclosed diisocyanate can be substituted with other bifunctional compounds. Examples of suitable bifunctional compounds include diglycidyl ethers, dialdehydes such as glutaraldehyde, aliphatic and aromatic dicyanates such as Bisphenol A dicyanate, and diamines such as ethylene diamine or hexamethylene diamine.

Both the polymer matrices cross-linked with urethane linkages and the polymer matrices cross-linked with acyl semicarbazide linkages demonstrate high equilibrium water content and good mechanical strength and are therefore suitable for biomedical applications such as wound dressings and implant materials. The hydrogel membranes from both types of cross-linked linkages are translucent and flexible films in the dry state. The urethane cross-linked membranes are generally more opaque and somewhat abrasive on the surface, from the presence of N-hydroxy succinimide liberated during the cross-linking reaction. In the dry state, the membranes have extremely high tensile strength and elongation.

When equilibrated with water, the membranes begin to swell almost instantaneously, with the equilibrium reached in less than one hour. The membranes are elastic in the swollen state, with tensile strength independent of the molecular weight of the poly(alkylene oxide) used.

The mechanical properties of the polymer matrices can be further improved by forming semi-IPN's with the matrices. A linear, preformed second polymer is entrapped within the polymer matrices, which second polymer is chosen to be biocompatible and to contribute to the mechanical properties of the polymer matrix. The second polymer need not be miscible with the polymers of the present invention. Stated another way, the semi-IPN's of the present invention can be formed from polymers that would not be physically blendable by any other means. Examples of second polymers suitable for use with the semi-IPN's of the present invention include poly(BPA carbonate), poly(desaminotyrosyl tyrosine hexyl ester carbonate), poly(lactic acid), poly(caprolactone), cellulose acetate, cellulose nitrate, poly(ethylene terephthalate) poly(styrene) and poly(methyl methacrylate), and the like.

Semi-IPN's can be prepared by either cross-linking reaction with both the polymers of Formulas I and III. The semi-IPN's are prepared by dissolving an equimolar amount of the second polymer in the organic solvent with the polymer of Formula I or III. The reaction then proceeds as described above, with respect to the preparation of polymer matrices cross-linked by either urethane or acyl semicarbazide linkages. The second polymer is then entrapped within the cross-linked polymer matrix, as the polymer matrix is formed.

Both the cross-linked polymer matrices and the semi-IPN's can be used as means for drug delivery when utilized as wound dressings or biomedical implants. The polymer matrices cross-linked by urethane linkages from the polymers of Formulas I and III are not cross-linked by means of their pendant functional groups, which remain available for drug attachment. The trifunctional amine can also be quaternized for the attachment of pharmaceutically active compounds. While the polymer matrices that are cross-linked by acyl semicarbazide linkages covalently bond with the diisocyanate by means of their pendant functional groups, not all pendant functional groups participate in the cross-linking, and an excess of polymer can also be utilized, so that pendant functional groups remain uncross-linked for drug attachment. Wound dressings prepared from hydrogel membranes or semi-IPN's of the polymer matrices can thus incorporate antibiotics to promote wound healing.

In view of the foregoing, it can be readily appreciated that the poly(alkylene oxide) copolymers of the present invention are versatile drug carriers derived from biocompatible components that are capable of being adapted to conjugate with a number of drug functional groups, so as not to be limited by drug structure or activity. The drug carriers can be administered in a variety of forms that are dominated by the desirable properties of the poly(alkylene oxides) from which the carriers are derived.

The following non-limiting examples set forth hereinbelow illustrate certain aspects of the invention. All parts and percentages are by weight unless otherwise noted, and all temperatures are in degrees Celsius.

EXAMPLES

Example 1

Preparation of PEG-bis Succinimidyl-Carbonate

The preparation of PEG-bis Succinimidyl Carbonate is disclosed in the above-incorporated U.S. Pat. application Ser. No. 340,928 by Zalipsky. In a 250 mL round-bottomed flask, 10 g (10 mmols of hydroxyl groups) of PEG 2000 (Fluka) was dissolved in 120 mL of toluene and the polymer solution was azeotropically dried for two hours under reflux using a Dean-Stark trap. The polymer solution was then cooled to 25° C. and 15 mL (29 mmol) of a 20 percent solution of phosgene in toluene (1.93 M) was added. The reaction mixture was stirred at 25° C. overnight and then evaporated to dryness on a rotary evaporator (water bath temperature maintained at 40° C.). Another 100 mL of toluene was added and evaporated to remove all traces of phosgene. To the polymeric chloroformate was added 30 mL of dry toluene, 10 mL of methylene chloride, and 1.7 g (14.8 mmol) of N-hydroxy succinimide, and the mixture was stirred vigorously. The reaction flask was then cooled in an ice water bath and 1.5 g (14.9 mmol) of triethylamine was added gradually. Immediate precipitation of triethylamine hydrochloride was seen. The cooling bath was removed and the stirring continued at 25° C. for five hours. Then 10 mL of toluene was added and the reaction mixture cooled to 4° C. to maximize the triethylamine hydrochloride precipitation.

The precipitate was filtered and the filtrate concentrated to about half of its original volume. The concentrated solution was then added to 60 mL of ether with stirring to precipitate the polymeric product. After cooling to 40° C., the crude product was recovered by filtration, dried, redissolved in 100 mL of 2-propanol at 45° C. and allowed to recrystallize. The product was recovered by filtration, washed with ether and dried under high vacuum. The recovery of the white crystal and solid was 74 percent.

Example 2

Preparation of PEG-Lysine Ethyl Ester Copolymer (Poly(PEG-Lys-OEt))

In a 500 mL three-necked round-bottomed flask fitted with an overhead stirrer was dissolved 1.1 g (4.4 mmol. of lysine ether ester hydrochloride salt (Fluka) and 1.7 g (21 mmol) of sodium bicarbonate in 100 mL of water. The PEG-N-hydroxy succinimide-dicarbonate of Example 1 (10 g, 4.4 meq) was dissolved in 200 mL of methylene chloride and added to the reaction mixture. The mixture was stirred vigorously (about 1100 rpm) for two hours and then acidified to about pH 2. The two phases were separated and the organic phase was washed twice with NaCl. The organic layer was then dried over anhydrous $MgSO_4$, filtered and concentrated. The polymer was precipitated using cold ether, cooled to 4° C. and filtered to recover 6.7 g (67 percent) of the polymer.

500 mg of the crude polymer was dissolved in 10 mL of distilled water and dialyzed against distilled water at room temperature for 48 hours using a SPECTRAPOR ™ membrane with a molecular weight cut-off of 12,000 to 14,000 daltons. The purified polymer was extracted with methylene chloride, washed with saturated NaCl solution, dried and evaporated to obtain 263 mg (53 percent) of pure polymer.

Example 3

Preparation of PEG-Lysine Copolymer (Poly(PEG-Lys)

5 g of the polymer of Example 2 was dissolved in 5 mL of $H_2O$. The pH of the polymer solution was about 5 as measured with a pH meter. A 0.01 N NaOH solution was prepared, and the base was added dropwise into the polymer solution with stirring. The pH was monitored continuously and kept around 11.5 by the addition of base as needed. The reaction was allowed to go for five hours. The reaction was stopped and the reaction mixture was acidified with 0.1 N HCl. The polymer was extracted into methylene chloride and the extract was washed with saturated NaCl, dried over anhydrous MgSO$_4$, filtered and concentrated. The polymer was then precipitated with cold ether. After cooling for several hours, the product was collected in a Buchner funnel, washed with cold ether and dried under vacuum overnight. 3.5 g of polymer (71 percent) was recovered.

Example 4

Preparation of Activated Poly(PEG-Lys)

In a 10 mL round-bottomed flask, 1.0 g (0.46 mmol) of the polymer of Example 3 was dissolved in 5 mL of methylene chloride. To this solution 0.26 g of N-hydroxy succinimide (Aldrich) (2.3 mmol) was added. The flask was cooled in an ice water bath and 0.10 g (0.50 mmol) of dicyclohexyl carbodiimide (DCC) (Aldrich) was added. The reaction mixture was then stirred at 0° C. for one hour and at room temperature overnight. The reaction mixture was filtered to remove dicyclohexyl urea and the methylene chlorine was evaporated to give a white, waxy material. To this 5 mL of isopropanol was added and the mixture was stirred until a clear solution was obtained. Cooling to −15° C. precipitated a white solid which was collected on a Buchner funnel and washed first with isopropanol and then with hexane. The material was further purified by recrystallization from isopropanol. The recovery of the final product was 0.72 g (71 percent).

Example 5

Preparation of Poly(PEG-Lys) with Pendant Acyl Hydrazaone Functional Groups In a 50 mL round-bottomed flask, 2.2 g (1.0 mmol) of the polymer of Example 3 was dissolved in 20 mL of methylene chloride. The flask was then cooled in an ice water bath. To the flask were added 410 mg (2.0 mmol) of DCC and 260 mg (2.0 mmol) of tert-butyl carbazate (Aldrich). The contents of the flask were stirred at ice water bath temperature for 1 hour and then stirred at room temperature for 24 hours. The reaction mixture was filtered to remove the dicyclohexyl urea, followed by evaporation of the filtrate to dryness, which gave 1.5 g of light solid that was purified by recrystallization from 2-propanol. $^1$H proton NMR spectrum of the white, waxy solid showed tert-butyl peaks, the area of which corresponded to greater than 90 percent conversion. When redissolved in methanol and reprecipitated with ether, the relative intensity of this peak did not decrease.

An approximate 4 M solution of HCl in dioxane was prepared by bubbling HCl gas through dioxane in an Erlenmeyer flask (a 4.0 M solution is also available commercially from (Pierce). In a 250 mL round-bottomed flask was placed 75 mL of the 4.0 M HCl/dioxane solution, and to this was added with stirring 5.0 g of the polymer-carbazate reaction product in the form of small pieces. Stirring was continued for two hours at room temperature. The polymer settled at the bottom of the flask as an oil. The dioxane/HCl layer was decanted out and the polymer layer was added to 100 mL of the ether with stirring. The polymer precipitated and was isolated, washed twice with 50 mL of ether and dried under vacuum. It was further precipitated by recrystallization from isopropanol.

The $^1$H NMR spectrum of the product showed the complete absence of tert-butyl groups. Non-aqueous titration against sodium methoxide with methyl red as the indicator showed about 100 percent of the expected hydrochloride.

Example 6

Preparation of Poly(PEG-Lys) Having Ethanol Amide Pendant Functional Groups In a 50 mL round-bottomed flask, 0.400 g (0.1819 mmol) of the poly(PEG-Lys) of Example 3 was dissolved in 40 mL of water. To this solution was added 0.1 mL (1.656 mmol) of ethanol amine (Aldrich). The pH was adjusted to 4.75 by the addition of 0.1 N HCl. Then 0.348 g (1.82 mmol) of solid 1-(3-dimethylaminopropyl-3-ethylcarbodiimide) (Sigma) was added. The pH had a tendency to increase, but was maintained around 4.75 by the addition of 1 N HCl. After 30 minutes, no further increase in pH was observed. The reaction mixture was stirred overnight and then acidified and extracted into methylene chloride. The methylene chloride extract was washed with saturated sodium chloride solution, dried with anhydrous magnesium sulfate, filtered, concentrated to a viscous syrup and precipitated with cold ether. About 0.318 g of crude poly(PEG-Lys) with ethanol amide pendant functional groups was recovered. The crude product was purified by reprecipitation from isopropanol, followed by washings with hexane and complete drying in vacuo. Thin layer chromatography (TLC) in a 4:1 ratio solution of ethanol to ammonia showed an absence of free ethanol amine.

Example 7

Preparation of Poly(PEG-Lys) Having Ethylamine Pendant Functional Groups

In a 100 mL three-necked flask, 1.21 g (0.55 mmol) of the poly(PEG-Lys) of Example 3 was dissolved in 80 mL of water. To this solution was added 0.37 mL (5.5 mmol) of ethylene diamine (Aldrich). The pH was adjusted to 4.75 by the addition of 1 N HCl. Then 1.05 g (5.5 mmol) of solid 1-(3-dimethylaminopropyl-3-ethylcarbodiimide) was added. The pH had a tendency to increase, but was maintained around 4.75 by the addition of 1 N HCl. After 30 minutes, no further increase in pH was observed. The reaction mixture was stirred overnight and then made basic and extracted into methylene chloride. The methylene chloride extract was washed with saturated sodium chloride, dried with anhydrous magnesium sulfate, filtered, concentrated to a viscous syrup and precipitated with cold ether. About 0.725 g of crude poly(PEG-Lys) having ethylamine pendant functional groups was recovered, which was purified by reprecipitation with isopropanol. TLC in a 2:1 solution of ethanol to ammonia showed absence of free diamine.

Example 8

Preparation of Poly(PEG-Lys) Having Pendant Hexylamine Functional Groups

The procedure of Example 7 was followed substituting 5.5 mmol of hexamethylene diamine (Aldrich) for the 5.5 mmol of the ethylene diamine. Upon purification of the product, TLC in a 2:1 ratio ethanol to ammonia solution showed absence of free diamine.

Example 9

Preparation of Poly(PEG-Lys)-Cephradine Drug Conjugate

In a 25 mL round-bottomed flask, 0.1523 g of cephradine (0.436 mmoles) (Sigma) was dissolved in a mixture of 4.5 mL water and 2 mL of dioxane. To this solution, 0.500 g of the activated poly(PEG-Lys) of Example 4 (0.218 mmoles) was added. This was followed by the addition of 0.055 g of NaHCO$_3$. The solution was stirred at room temperature. The pH of the reaction was monitored and was found to remain in the narrow range from about 7.0 to 7.5. The reaction mixture was neutralized after one hour by adding a few drops at 0.1 N HCl and extracted into methylene chloride. The extract was washed with saturated sodium chloride, dried over anhydrous magnesium sulfate, filtered and concentrated. The polymer was then precipitated with cold ether. After cooling for several hours, the product was collected on a Buchner funnel, washed with cold ether and dried under vacuum overnight. The recovery was 0.355 g, or 71 percent.

The reaction product was then dissolved in water (50 mg/mL) and dialyzed against distilled water at room temperature using a SPECTRAPOR TM membrane having a molecular weight cutoff of 12,000 to 14,000 daltons. After 24 hours the product was isolated by lyophilization.

Examples 10–12

Attachment of Cephradine to Poly(PEG-Lys); Optimization of Conditions

Example 9 was repeated at pH's of 7.2 and 8.5, reaction times of 1.5 and 3 hours, and polymer to drug ratios of 1:1. The mole-percent degree of drug attachment was determined by iodometric assay, which method measures only the active drug. As shown in Table I, the greatest degree of drug attachment was obtained with the conditions of Example 9, namely, a reaction time of 1 hour, a pH of 7.5 and a ratio of polymer to drug of 1:2.

TABLE I

| Example | Time | pH | Polymer:Drug Ratio | Degree of Attachment[1] |
|---|---|---|---|---|
| 9 | 1 | 7.5 | 1:2 | 61.5 |
| 10 | 3 | 8.5 | 1:1 | 41.5 |
| 11 | 1.5 | 8.5 | 1:1 | 40 |
| 12 | 1.5 | 7.2 | 1:1 | 50 |

[1]Mole %

Table I shows that decreasing the reaction time from 3 to 1.5 hours had no significant effect on the degree of drug attachment. This is expected because the active ester would not be stable under the conditions of the reaction for a long period of time. Also, the amount of active drug on the polymer is higher when the reaction is done at a lower pH. Because the iodometric assay is specific for active drug, this could mean that at a pH of 8.5 some of the beta-lactam units of the drug may have been hydrolyzed. Thus, the optimum reaction conditions appear to be mild enough to prevent significant cleavage of the beta-lactam ring while at the same time giving a high degree of conjugation.

Example 13

Preparation of a Poly(PEG-Lys)-Penicillin V Drug Conjugate

In a 10 mL round-bottomed flask, 0.400 g (0.178 mmol) of the poly(PEG-Lys) having ethanolamide pendant functional groups of Example 6 was dissolved in 4 mL of methylene chloride. To this solution was added 0.094 g (0.267 mmol) of Penicillin V (Sigma) and 0.008 g (0.065 mmol) of dimethylaminopyridine (Aldrich). The reaction mixture was cooled in an ice water bath and then 0.048 g (0.232 mmol) of DCC was added. After a few hours at 0° C., the reaction vessel was moved to a cold room maintained at 420 C. and allowed to stir for almost six days. A precipitate of dicyclohexyl urea formed and was removed by filtration. The drug conjugate was precipitated with cold ether. About 0.250 g of crude product was obtained which was purified by reprecipitation twice from isopropanol. TLC in methanol showed absence of free drug.

Example 14

Preparation of Poly(PEG-Lys)-Acyclovir Conjugate

Acyclovir succinate is prepared by heating a solution of 0.2252 g of acyclovir (1 mmol) (Sigma), 0.200 g of succinic anhydride (2 mmoles) (Aldrich) and 0.14 mL of triethylamine in 15 mL of dry dimethylformamide at 60° C. in an oil bath for 21 hours. The solution was then cooled and the volatile constituents were evaporated in vacuo, and the residue was taken up in 8 mL of ice water and acidified to pH 2 with 2 N HCl. A white precipitate was formed that was collected by filtration, thoroughly washed with ice water and dried in vacuo over P$_2$O$_5$ at 40° C. to yield 0.180 g (54 percent) of the product. The ester was then recrystallized from methanol and characterized by IR and $^1$H NMR spectroscopy.

In a 10 mL round-bottomed flask, 0.287 g (0.133 mmol) of the poly(PEG-Lys) having acyl hydrazine pendant functional groups of Example 5 and 0.036 g (0.111 mmol) of the acyclovir succinate were dissolved in 5 mL of anhydrous pyridine. The reaction mixture was cooled in an ice water bath and then 0.025 g (0.121 mmol) of DCC was added. After initial cooling for about one hour, the reaction was allowed to stir for almost three days at room temperature. The dicyclohexyl urea that precipitated was removed by filtration and the product was transferred to a separatory funnel to which 10 mL of water was added and the product was extracted with methylene chloride. The methylene chloride extract was washed with saturated sodium chloride solution, dried, concentrated and precipitated with ether. About 0.140 g of product was recovered that was purified by extraction with isopropanol. TLC in a 4:1 ratio solution of ethanol to acetic acid showed the absence of free acyclovir succinate.

Example 15

Preparation of N-Benzylcarbamate Derivative of a Copolymer of PEG and Glutamic Acid 2 g of PEG 2000 was azeotropically dried following the procedure of Example 1 by dissolving the polymer in 30 mL of toluene in a pre-weighed 50 mL round-bottomed flask provided with a stirrer. The polymer solution was azeotropically dried for two hours under reflux in an oil bath, the temperature of which was maintained at 140° C. All the solvent was distilled off and the product was dried under vacuo. The dried PEG was reweighed, dissolved in 5 mL of methylene chloride and stirred under argon. An equimolar amount of glutamic acid, the N-terminal of which was protected by a benzylcarbamate functional group (Sigma) was added. Four times this amount of diisopropylcarbodiimide (Aldrich) and four times this amount of dimethylaminopyridinium toluene sulfonate (Aldrich) were added. The reaction mixture was heated slightly to dissolve the glutamic acid. The reaction was allowed to run for 24 hours at room temperature with stirring. A urea precipitate formed that was removed by filtration, and the product was precipitated by cold ether, filtered and dried under vacuum. About 1.6 g of polymer was recovered, which was purified by reprecipitation from isopropanol. TLC in a 5:5:1 ratio solution of toluene to acetic acid to water showed the absence of free glutamic acid.

Example 16

Preparation of Poly(PEG-Lys) Membranes Cross-Linked by Hexamethylene Diisocyanate A mold was prepared by clamping two square glass plates together, one of which had a 5 cm diameter circular cavity. The contacting surfaces of the glass plates were coated with trimethylchlorosilane (Aldrich) to prevent adhesion. The mold was placed on a level surface inside a glove box and further leveled using a carpenter's level. In a 100 mL beaker, 1.5 g of the poly(PEG-Lys) having pendant acyl hydrazine groups (0.67 mmol of hydrazine groups) of Example 5 was dissolved in 40 mL of methylene chloride. To this solution was added 1.5 g finely powdered sodium bicarbonate. The suspension was stirred for one hour and the supernatant was tested for the presence of chloride ions with silver nitrate. A few drops of the methylene chloride solution were placed into a test tube, the methylene chloride was evaporated, and the residue was reacted with a few drops of silver nitrate solution acetified with nitric acid. The absence of any white turbidity indicated the complete neutralization and removal of hydrochloric acid.

The solution was then filtered and the residue was washed with methylene chloride. To the combined filtrate, 54 microliters of hexamethylene diisocyanate (56 mg, 0.67 meq of isocyanate groups) (Aldrich) was added with stirring. After two to three minutes of stirring, the solution was poured into the circular cavity of the solvent casting mold. The cavity of the mold was covered with filter paper so that the solvent evaporation was slow and uniform. The film was allowed to dry in the glove box for 48 hours and then peeled from the mold. The thickness of the membrane was measured with an electronic vernier caliper inside the glove box and was found to be about 0.1 mm.

The membranes obtained were semi-transparent and were somewhat hygroscopic, curling up when exposed to moisture in ambient air. When placed in water, the size of the films doubled in all dimensions, indicating a very large, swelling ratio. The swollen membranes were transparent.

The membrane was assayed with trinitrophenyl sulfonic acid (TNBS) (Fluka) to determine the extent of cross-linking. An excess of TNBS was used, and after reacting with the polymer, the unreacted TNBS was allowed to react with an excess of adipic hydrazide. The IR absorbance obtained at 500 nm was then used to calculate the amount of free hydrazides present on the cross-linked membrane. Using this method, it was found that 80-85 percent of all available hydrazides precipitated in cross-linking, leaving only 15-20 percent of unreacted hydrazides on the cross-linked membrane.

Differential Scanning Calorimietry of the cross-linked membrane showed a sharp endothermic transition at 33.4° C. This is very similar to the Tm of the corresponding non-cross-linked poly(PEG-Lys) having pendant acyl hydrazine functional groups (34.1° C.). When the membrane was heated in an oven above the phase transition temperature, it became very flexible but did not disintegrate. These results indicate that the properties of PEG dominate even after copolymerization with lysine and cross-linking.

Swelling measurements of the membrane were made by two methods. The dimensions of the dry membrane was measured and the membrane was allowed to swell in water. The increase in dimension was taken as a measure of swelling. Alternatively, the membrane was weighed before and after swelling and the increase in weight was taken as a measure of swelling. Both methods indicated that the membrane absorbs about 5 to 8 times its weight of water.

Preliminary diffusion measurements were made using a small dialysis cell, p-nitroaniline was used as the diffusing solute. The membrane was used as a partition between an aqueous solution of p-nitroaniline and distilled water placed in the two compartments of the dialysis cell. The absorbance in the two compartments was measured as a function of time. These preliminary measurements showed that the rate of diffusion across cross-linked Poly(PEG-Lys) membranes was comparable to that of a regenerated cellulose of similar thickness.

The tensile strength of the membrane was measured using strips of membrane 0.07 mm thick, 5 mm wide and 50 mm long. Measurements were made employing both dry and swollen membranes, the results of which are shown in Table II.

TABLE II

| Membrane | Tensile at Yield (MPa) | Strength at Break (MPa) | Young's Modulus (MPa) | Elongation at Break (%) |
|---|---|---|---|---|
| Swollen | N/A | 0.46 | 0.62 | 73 |
| Dry | 8 | 64 | 19 | 350 |

In the swollen state, the membrane behaved like a perfect elastomer. The membrane did not exhibit a yield point and a plot of stress against strain gave a straight line in accordance with Hooke's Law. This elastic behavior should make them ideal materials for wound dressing and use applications.

The stability of the membrane was investigated in acidic, basic and neutral media, the results of which are listed in Table III below. Small specimens of the membrane were placed in contact with a number of aqueous solutions of varying pH at room temperature and the time required for the complete disappearance of the membrane was noted. The membrane was generally found to be more stable in weakly acidic media and extremely unstable in alkaline media.

TABLE III

| SOLUTION | TIME REQUIRED FOR DISAPPEARANCE |
|---|---|
| 1 N HCL | 5 to 8 days |

TABLE III-continued

| SOLUTION | TIME REQUIRED FOR DISAPPEARANCE |
|---|---|
| 0.1 N HCL | No change in 8 days |
| 0.01 N HCL | No change in 8 days |
| Deionized water | No change in 8 days |
| Borate (pH = 9) | 5 to 8 days |
| 0.01 N NaOH | Less than 5 hours |
| 0.1 N NaOH | Less than 5 hours |
| 1 N NaOH | Less than 1 hour |

To test the stability under physiological conditions, an accelerated stability study was performed in which samples of membrane were exposed to phosphate buffer of pH 7.4 at 60° C. As depicted in FIG. 1, under these conditions, the membrane lost weight at the rate of about 1 percent per hour. After 60 hours, the membrane disintegrated and became soluble in the buffer.

Example 17

Preparation of Electrically Conductive Materials

A 10 percent solution in freshly distilled tetrahydrofuran was prepared of a mixture of lithium triflat (Aldrich) and the poly(PEG-Lys-OEt), prepared according to the procedure described in Example 2, in a polymer-electrolyte ratio of 4:1 by weight. The polymer had a weight-average molecular weight of 140,000 daltons. A film was cast from the solution as described above with respect to Example 16. A sticky film was obtained that was scraped from the glass plates, dried under high vacuum, and pressed into pellets at a pressure of 0.15 ton and a temperature of 27.C. This resulted in the formation of clear pellets.

Conductivity was measured using a 70 mg pellet having a thickness of 0.5 mm and a 300 mg pellet having a thickness of 2.0 mm. The conductivity of the pellets was evaluated using standard, established techniques. First, conductivity was measured under high vacuum without exposing the pellets to ambient conditions. The conductivity of both pellets was found to be essentially identical, and in the order of $10^{-3}$ ohm$^{-1}$cm$^{-1}$. This is relatively high value that is close to the threshold needed for commercial applications. However, when the same samples were examined in ambient air, the conductivity increased to $10^{-1}$ ohm$^{-1}$cm$^{-1}$, a significant increase.

Figure 2:
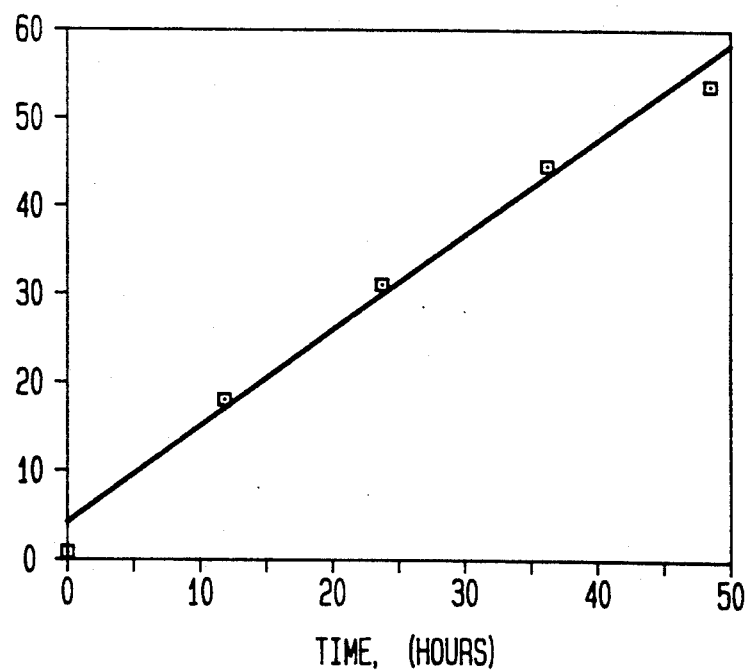
FIG. 2 depicts an Arrhenius plot of conductivity versus temperature for an ionically conductive material of the present invention.

The temperature dependance of the ionic conductivity of the polymer was then measured between room temperature and 40° C., which is near the melting point of the polymer. An Arrhenius plot of conductivity vs. temperature (° K.) is shown in FIG. 2. Conductivity increases with increasing temperature until the polymer becomes molten, at which point conductivity remains constant as temperature increases.

Example 19

Preparation of Poly(PEG-Lys) Membranes Cross-Linked with Tris(Aminoethyl) Amine

In a 100 mL beaker, 1.87 g of the PEG-bis(Succinimidyl Carbonate) of Example 1 was dissolved in 20 ml of methylene chloride. In another beaker, 82 microliters (89 mg) of tris(aminoethylamine) was dissolved in 20 ml of methylene chloride. The triamine solution was added to the PEG solution with vigorous stirring. After about five minutes, films were cast of the solution following the procedure described above with respect to Example 16.

Swelling measurements of the membrane were made by the two methods described above with respect to Example 16. Both methods indicated that the membrane absorbed about six times its weight of water.

The stability of the membrane was investigated in acidic, basic and neutral media, as described above with respect to Example 16. In sodium hydroxide (0.01 and 0.1 N) the membrane disintegrated within a few hours. In acidic media and in phosphate buffer (pH 7.4) the membrane appeared to be stable for longer periods of time. The accellerated degradation study of Example 16 was also performed, in which the membrane remained intact for more than a week. An analysis of the buffer in which the accellerated stability study was conducted revealed that during the first 24 hours a small amount of PEG chains had leached from the cross-linked membrane, but throughout the following 72 hours, no more PEG was leached.

Example 19

Preparation of Poly(Caprolactone) Semi-IPN's of Poly(PEG-Lys) Membranes Cross-Linked by Diisocyanetohexane The poly(PEG-Lys) membrane cross-linked by diisocyanetohexane was prepared as in Example 16, using 210 mg of the poly(PEG-Lys) of Example 5 having acyl hydrazine functional groups, dissolved in 10 mL of methylene chloride. The free base was formed with sodium bicarbonate, and the solution was then filtered. Prior to the addition of four microliters (3.9 mg) of the hexamethylene disocyanate, 0.47 g of poly(caprolactone) (Union Carbide); (mw 72,000) was added to the filtrate, which was stirred for 30 minutes to dissolve the polymer completely. The poly(PEG-Lys) was cross-linked and films were cast following the procedure described above with respect to Example 16. The resulting membrane was hydrophilic and absorbed water with an equilibrium water content of 36%, whereas film made of poly(caprolactone) alone is hydrophobic.

As will be readily appreciated, numerous variations and combinations of the features set forth above can be utilized without departing from the present invention as set forth in the claims. Such variations are not regarded as a departure of the spirit and scope of the invention, and all such modifications are intended to be included within the scope of the following claims.

What is claimed is:

1. A polymer comprised of one or more recurring structural units independently represented by the formula:

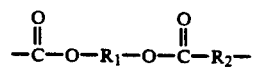

wherein $R_1$ is a poly(alkylene oxide) copolymerized with $R_2$, which is an amino acid or peptide sequence containing two amino groups and at least one pendant carboxylic acid group.

2. The polymer of claim 1, wherein $R_2$ is an amino acid or peptide sequence represented by the formula:

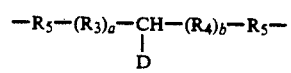

wherein R₃ and R₄ are independently selected from the group consisting of saturated and unsaturated, straight-chained and branched alkyl groups containing up to 6 carbon atoms and alkyl phenyl groups, the alkyl portions of which are covalently bonded to an amine and contain up to 6 carbon atoms; and a and b are independently zero or one;

R₅ is —NH— or —NH—AA—, wherein —AA— is an amino acid or peptide sequence, with the proviso that —AA— has a free N-terminus;

D is a pendant functional group selected from the group consisting of:

wherein, when D is

Y is selected from the group consisting of —OH, —NH—NH₂, 'O—R₆—NH₂, —O—R₆—OH, —NH—R₆—NH₂, —NH—R₆—OH,

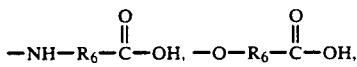

a C-terminus protecting group and a derivative of a pharmaceutically active compound covalently bonded to said pendant functional group by means of:

an amide bond in the case where in the underivatized pharmaceutically active compound a primary or secondary amine is present at the position of the amide bond in the derivative; or an ester bond in the case where in the underivatized pharmaceutically active compound a primary hydroxyl is present at the position of the ester bond in the derivative; and when D is:

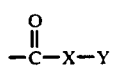

Y is a derivative of a pharmaceutically active compound covalently bonded to said pendant functional group by means of X, wherein X is a linkage selected from the group consisting of:

(a) —NH—NH— in the case where in the underivatized pharmaceutically active compound an aldehyde or ketone is present at the position linked to said pendant functional group by means of X;

(b) —NH—NH—, —NH—R₆—NH—, —O—R₆—NH—, —O—R₆—O— or —NH—R₆—O— in the case where in the underivatized pharmaceutically active compound a carboxylic acid is present at the position linked to said pendant functional group by means of X; and

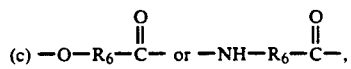

in the case where in the underivatized pharmaceutically active compound the primary or secondary amine or primary hydroxyl group is present in the position linked to said pendant functional group by means of X;

and R₆ is selected from the group consisting of alkyl groups containing from two to six carbon atoms, alpha-, beta-, gamma- and omega amino acids, and peptide sequences.

3. The polymer of claim 1, wherein said poly(alkylene oxide) is selected from the group consisting of polyethylene glycol, polypropylene glycol, poly(isopropylene glycol), polybutylene glycol, poly(isobutylene glycol) and copolymers thereof.

4. The polymer of claim 3, wherein said poly(alkylene oxide) has the structure:

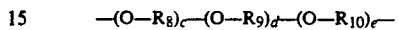

wherein R₈, R₉ and R₁₀ are independently selected from the group consisting of straight-chained and branched alkyl groups containing up to four carbon atoms; and c is an integer between about 1 and about 100, inclusive, and d and e are independently integers between 0 and about 100, inclusive, with the proviso that the sum of c, d and e is between about 10 and about 100, inclusive.

5. The polymer of claim 3, wherein said poly(alkylene oxide) comprises polyethylene glycol.

6. The polymer of claim 2, wherein R₃ and R₄ are independently selected from the group consisting of alkyl groups containing between 1 and 6 carbon atoms.

7. The polymer of claim 2, wherein either a or b is zero.

8. The polymer of claim 2, wherein R₅ is —NH—.

9. The polymer of claim 2, wherein Y is —NH—NH₂.

10. The polymer of claim 2, wherein R₂ comprises a natural amino acid.

11. The polymer of claim 2, wherein Y is a C-terminus protecting group selected from the group consisting of alkyl, aryl and silicon protecting groups.

12. The polymer of claim 2, wherein Y comprises a derivative of a pharmaceutically active compound selected from the group consisting of acyclovir, cephradine, melphalan, procaine, ephedrine, adriamycin and daunomycin and linked to said pendant functional group by means of an amide bond at a position on said pharmaceutically active compound occupied in the underivatized form of said pharmaceutically active compound by a primary or secondary amine.

13. The polymer of claim 2, wherein Y comprises a derivative of a pharmaceutically active compound selected from the group consisting of acyclovir, plumbagin, atropine, quinine, digoxin and quinidine and linked to said pendant functional group by means of an ester bond at a position on said pharmaceutically active compound occupied in the underivatized form of said pharmaceutically active compound by a primary hydroxyl.

14. The polymer of claim 2, wherein Y comprises derivative of a pharmaceutically active compound selected from the group consisting of adriamycin, daunomycin and testosterone and linked to said pendant functional group by means of —X— at a position on said pharmaceutically active compound occupied in the underivatized form of said pharmaceutically active compound by an aldehyde or ketone; and —X— comprises —NH—NH—.

15. The polymer of claim 2, wherein Y comprises a derivative of a pharmaceutically active compound selected from the group consisting of chlorin e₆, cephradine, cephalothin, melphalan, penicillin V, nicotinic acid, chemodeoxycholic acid and chlorambucil and linked to said pendant functional group by means of —X— at a position on said pharmaceutically active compound occupied in the underivatized form of said pharmaceutically active compound by a carboxylic acid; and X is selected from the group consisting of —NH—NH—, —NH—$R_6$—NH—, —O—$R_6$—NH—, —O—$R_6$—O— and —NH—$R_6$—O—.

16. The polymer of claim 2, wherein Y comprises a derivative of a pharmaceutically active compound selected from the group consisting of acyclovir, cephradine, malphalan, plumbagin, procaine, ephedrine, adriamycin, daunomycin, atropine, quinine, digoxin and quinidine and linked to said pendant functional group by means of —X— at a position on said pharmaceutically active compound occupied in the underivatized form of said pharmaceutically active compound by a primary or secondary amine or primary hydroxyl, and —X— is selected from the group consisting of:

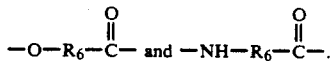

17. The polymer of claim 2, wherein Y comprises a derivative of an oxidized monoclonal antibody covalently linked to said pendant functional group by means of —X— at a position on said monoclonal antibody occupied in the underivatized form of said oxidized monoclonal antibody by a ketone or aldehyde, and X is selected from the group consisting of —NH—NH—, —$NH_6$—NH— and —O—$R_6$—NH—.

18. The polymer of claim 17, wherein said polymer comprises said recurring structural units in which Y is a pharmaceutically active compound co-conjugated with said monoclonal antibody.

19. The polymer of claim 18, wherein the ratio of said pharmaceutically active compound conjugated on said polymer and said monoclonal antibody conjugated on said polymer is between about 4 and about 100.

20. The polymer of claim 19, wherein said pharmaceutically active compound comprises chlorin $e_6$ and said monoclonal antibody comprises an anti-T cell monoclonal antibody.

* * * * *

UNITED STATES PATENT AND TRADEMARK OFFICE
CERTIFICATE OF CORRECTION

PATENT NO. : 5,219,564
DATED : June 15, 1993
INVENTOR(S) : Zalipsky et al.

It is certified that error appears in the above-identified patent and that said Letters Patent is hereby corrected as shown below:

On the title page, under the heading "[75] Inventors:" "Durgadas bolikal" should read --Durgadas Bolikal--.

Column 2, line 27, "Chem. Raoid Commun." should read --Chem Rapid Commun.--.

Column 13, line 23, after "one or" insert --more natural amino acids.--.

Column 35, line 36, in the title of Example 5, "Hydrazaone" should read --Hydrazine--.

Column 38, line 15, "420°C" should read --4°C--.

Column 41, line 32, "27.C" should read --27°C--.

Column 41, line 56, "Example 19" should read --Example 18--.

Column 43, line 24, "'O-$R_6$-$NH_2$," should read -- -O-$R_6$-$NH_2$,--.

Signed and Sealed this

First Day of March, 1994

Attest:

BRUCE LEHMAN

*Attesting Officer*  *Commissioner of Patents and Trademarks*